United States Patent
Levitzki et al.

(10) Patent No.: US 11,912,747 B2
(45) Date of Patent: Feb. 27, 2024

(54) CHIMERIC PROTEINS FOR TARGETING DSRNA

(71) Applicant: TARGIMMUNE THERAPEUTICS AG, Basel (CH)

(72) Inventors: Alexander Levitzki, Jerusalem (IL); Yael Langut, Haifa (IL)

(73) Assignee: TARGIMMUNE THERAPEUTICS AG, Basel (CH)

( * ) Notice: Subject to any disclaimer, the term of this patent is extended or adjusted under 35 U.S.C. 154(b) by 1207 days.

(21) Appl. No.: 16/329,577

(22) PCT Filed: Dec. 15, 2016

(86) PCT No.: PCT/IL2016/051341
§ 371 (c)(1),
(2) Date: Feb. 28, 2019

(87) PCT Pub. No.: WO2018/042411
PCT Pub. Date: Mar. 8, 2018

(65) Prior Publication Data
US 2019/0194282 A1 Jun. 27, 2019

Related U.S. Application Data

(60) Provisional application No. 62/383,466, filed on Sep. 4, 2016.

(51) Int. Cl.
| | |
|---|---|
| C07K 14/47 | (2006.01) |
| C12N 15/117 | (2010.01) |
| A61P 35/00 | (2006.01) |
| A61K 47/68 | (2017.01) |
| C07K 16/30 | (2006.01) |
| C12N 15/62 | (2006.01) |
| A61K 38/00 | (2006.01) |

(52) U.S. Cl.
CPC ...... *C07K 14/4748* (2013.01); *A61K 47/6851* (2017.08); *A61P 35/00* (2018.01); *C07K 16/3069* (2013.01); *C12N 15/117* (2013.01); *C12N 15/62* (2013.01); *A61K 38/00* (2013.01); *A61K 47/68* (2017.08); *A61K 47/6869* (2017.08); *C07K 2317/622* (2013.01); *C07K 2317/77* (2013.01); *C07K 2319/60* (2013.01); *C07K 2319/85* (2013.01); *C12N 2310/17* (2013.01); *C12N 2320/32* (2013.01)

(58) Field of Classification Search
CPC ............ C07K 14/4748; C07K 16/3069; C07K 2317/622; C07K 2317/77; C07K 2319/60; C07K 2319/85; A61K 47/6851; A61K 38/00; A61K 47/68; A61K 47/6869; A61P 35/00; C12N 15/117; C12N 15/62; C12N 2310/17; C12N 2320/32
See application file for complete search history.

(56) References Cited

U.S. PATENT DOCUMENTS

| | | | |
|---|---|---|---|
| 9,006,406 B2 | 4/2015 | Levitzki et al. | |
| 10,543,232 B2 | 1/2020 | Levitzki et al. | |
| 2015/0174265 A1 | 6/2015 | Wittrup et al. | |
| 2016/0222072 A1* | 8/2016 | Gao | C12N 15/87 |
| 2018/0346596 A1 | 12/2018 | Levitzki | |

FOREIGN PATENT DOCUMENTS

| | | | | |
|---|---|---|---|---|
| EP | 2277542 A1 * | 1/2011 | ............. | A61K 45/06 |

OTHER PUBLICATIONS

Langut et. al, Novel Targeted Therapy for Prostate Cancer, The Fifth Annual Meeting of the Israel Society for Research, published May 23, 2013 (Year: 2013).*
Ngo et al., in the Protein Folding Problem and Tertiary Structure Prediction, 1994 (Year: 1994).*
Hakan Mellstedt EJC Supplements II,, 2013, 3, pp. 1-11 (Year: 2013).*
Langut Y et al., PSMA-homing dsRNA chimeric protein vector kills prostate cancer cells and activates anti-tumor bystander responses. Oncotarget. Apr. 11, 2017;8(15):24046-24062. (Year: 2017).*
Sengupta S et al., Comparison of prostate-specific membrane antigen ligands in clinical translation research for diagnosis of prostate cancer. Cancer Rep (Hoboken). Aug. 2019;2(4):e1169. (Year: 2019).*
Gal-Ben-Ari S, Barrera I, Ehrlich M, Rosenblum K. PKR: A Kinase to Remember. Front Mol Neurosci. Jan. 9, 2019;11:480. (Year: 2019).*
Leninger et al. (Elife. 2019;8:e48909. Published Oct. 22, 2019) (Year: 2019).*
Zekri L et al., An IgG-based bispecific antibody for improved dual targeting in PSMA-positive cancer. EMBO Mol Med. Feb. 5, 2021;13(2):e11902. (Year: 2021).*
Joshi SR. Biosimilar peptides: need for pharmacovigilance. J Assoc Physicians India. Apr. 2011;59 Suppl:44-7. (Year: 2011).*
Murphy et al. Journal of Immunological Methods, vol. 463, p. 127-133, 2018 (Year: 2018).*
International Search Report issued in International Application No. PCT/IL2016/051341, dated Mar. 23, 2017.
Dar et al., "Conformation-dependent binding and tumor-targeted delivery of siRNA by a designed TRBP2: Affibody fusion protein," Nanomedicine: Nanotechnology, Biology, and Medicine 11:1455-1466 (2015).
Langut Y. et al., "Novel targeted therapy for prostate cancer," 5th Annual Meeting of the Israel Society for Cancer Research, May 23, 2013, p. 78.
Non-final Office Action issued in U.S. Appl. No. 15/915,770 dated May 7, 2021.

(Continued)

*Primary Examiner* — Julie Wu
*Assistant Examiner* — John J Skoko, III
(74) *Attorney, Agent, or Firm* — MEDLER FERRO WOODHOUSE & MILLS PLLC

(57) ABSTRACT

Described herein are recombinant chimeric proteins comprising a double stranded RNA (dsRNA) binding domain and a cancer-cell targeting domain for targeting of dsRNA to cancer cells. Methods of use of the described chimeric proteins are also provided herein.

20 Claims, 7 Drawing Sheets
Specification includes a Sequence Listing.

(56) References Cited

OTHER PUBLICATIONS

Dar et al., "Conformation-dependent Binding and Tumor-Targeted Delivery of siRNA by a Designated TRBP2: Affibody Fusion Protein," Nanomedicine: Nanotechnology, Biology and Medicine, 11(6): 1455-1466 (2015).
Langut et al., "Novel Targeted Therapy for Prostate Cancer," The Fifth Annual Meeting of the Israel Society for Cancer Research, p. 70 (2013). Accessible online: http://events.eventactcom/programview/ViewAbstract.aspx?Abst=36480&Codes 1040194.
Niikura et al., "Endosomal Escape Efficiency of Fusogenic B18 and B55 Peptides Fused with anti-EGFR Single Chain Fvas Estimated by Nuclear Translocation," J. Biochem. 159(1): 123-132 (2015).
International Search Report issued in PCT/IL2016/051341, dated Mar. 23, 2017.
Non-final Office Action issued in U.S. Appl. No. 15/915,770 dated Jan. 7, 2020.
Final Office Action issued in U.S. Appl. No. 15/915,770 dated Jun. 8, 2020.

\* cited by examiner

CHIMERIC PROTEINS FOR TARGETING DSRNA

REFERENCE TO AN ELECTRONIC SEQUENCE LISTING

The contents of the electronic sequence listing (0192-0054US2_Sequence Listing.txt; Size: 20 KB; and Date of Creation: Feb. 28, 2019) is herein incorporated by reference in its entirety.

CROSS REFERENCE TO RELATED APPLICATIONS

Benefit is claimed to U.S. Provisional Patent Application No. 62/383,466, filed Sep. 4, 2016, the contents of which are incorporated by reference herein in their entirety.

FIELD

Provided herein are recombinant chimeric proteins comprising a double stranded RNA (dsRNA) binding domain and a cancer-cell targeting domain for targeting of dsRNA to cancer cells. Methods of use of the described chimeric proteins are also provided herein.

BACKGROUND

Prostate cancer is the second most commonly diagnosed cancer worldwide, accounting for over 25% of new cancer cases diagnosed annually among men in the US (1). In the case of metastatic prostate cancer, patients are mostly treated with androgen deprivation therapy (ADT).

While this therapy generally achieves a short-term remission, patients typically develop castration-resistant prostate cancer (CRPC). There is a great demand for novel therapies for CRPC patients, as these patients rarely respond to existing therapies and demonstrate median survival of about 3 years (1-3).

Most targeted cancer therapies today delay but rarely prevent tumor progression. As tumor cells are genomically unstable, they eventually acquire mutations and genetic alterations that allow them to evade the therapy and develop resistance. The rate of killing that is elicited by targeted agents is too slow, providing the tumors with sufficient time to adapt to the constant pressure exerted on them by the therapy. Additionally, tumors are heterogeneous and possess a number of different subpopulations. Targeted therapies usually target only some of these subpopulations and not others, and therefore cannot be expected to eradicate the entire tumor.

Metastatic CRPC typically presents a unique cell surface molecule that can be exploited for targeted therapy: prostate-specific membrane antigen (PSMA). PSMA is over-expressed at levels of up to 1000-fold at all Gleason scores (4), while over-expression increases with tumor progression (5,6). Despite the heterogeneous nature of the disease, primary tumors or metastases that are completely PSMA-negative are rare (7). While the above findings support the notion that PSMA is a highly promising therapeutic target, no PSMA-targeted therapies are currently approved for clinical use. However, few agents are in clinical trials (8-11). Thus a continuing need exists for targeted therapy for CPRC.

SUMMARY

Described herein is an improved approach to the targeting of dsRNA to cancer cells, namely, the generation of a chimeric protein molecule that can deliver dsRNA to PSMA over-expressing cells.

The present disclosure provides a chimeric recombinant protein and encoding nucleic acids thereof which includes a double stranded RNA (dsRNA) binding domain; and a target binding moiety that binds to prostate surface membrane antigen (PSMA).

Additionally described is a complex that includes a described chimeric recombinant protein and dsRNA. Also described are uses of the described complexes in treatment of prostate cancer or inhibition of the development of tumor neovasculature, and corresponding methods of treatment of prostate cancer or inhibition of tumor neovasculature that include administering to a subject in need thereof a therapeutically effective amount of the described complex.

The foregoing and other objects, features, and advantages will become more apparent from the following detailed description, which proceeds with reference to the accompanying figures.

BRIEF DESCRIPTION OF THE DRAWINGS

FIG. 1A: Schematic representation of GFP-SCP. FIG. 1B: LNCaP, PC3 and MCF7 cells were incubated with 25 nM GFP-SCP for 5 hr. The cells were fixed and stained with anti-GFP antibody (Cy3) and 4, 6-diamidino-2-phenylindole and viewed by laser scanning confocal microscopy. FIG. 1C: LNCaP and MCF7 cells were incubated with GFP-SCP, then subjected to flow cytometric analysis. FIG. 1D: Upper panel: LNCaP cells were monitored by laser confocal imaging, 0 to 72 min after the addition of 200 nM GFP-SCP. Sulforhodamine-B was added to the medium immediately before adding the GFP-SCP, to mark the outside of the cells. Lower panel shows GFP fluorescence inside the cell, as measured using ImageJ.

FIG. 2A: Schematic representation of dsRB-SCP. FIG. 2B: Expression and purification of dsRB-SCP: L: Cleared lysate, M: Molecular weight marker, E1: Eluate following IMAC (nickel sepharose column), E2: Purified dsRB-SCP eluted from IEX (Ion exchange column). Dashed lines indicate where the picture of the gel was cut and reorganized. FIG. 2C: Binding of dsRB-SCP to dsRNA: dsRB-SCP (0.5-3 µg) was preincubated with 500 bp long dsRNA and electrophoresed on a 2% agarose gel. M: 100 bp DNA molecular weight marker.

FIG. 3A: Cells were seeded in triplicate, grown overnight, and treated as indicated for 100 hr. Viability was quantified using the CellTiter-Glo Luminescent Cell Viability Assay (Promega). FIG. 3B: Surviving cells remained permanently arrested. Cells were seeded in triplicate, grown overnight, and treated as indicated. Medium was replaced and viability was quantified after 100/172/344 hr using CellTiter-Glo. (Control cells were unable to proliferate beyond 2.5 doublings because they had reached full confluence). FIG. 3C: LNCaP cells were treated for the indicated times with dsRB-SCP/polyIC or polyIC alone, lysed and subjected to western blot analysis to detect full-length and cleaved Caspase-3 and PARP.

FIGS. 4A and 4B: LNCaP cells were treated as indicated for 48 hr, after which medium was collected and IP-10 and RANTES cytokines were measured by ELISA assays. FIG. 4C: LNCaP cells were treated as indicated for 4 h and IFN-β transcription was measured by qRT-PCR. FIG. 4D: dsRB-SCP/polyIC induces chemotaxis of PBMCs. LNCaP cells were grown and treated as indicated. 48 hr after treatment, the cell medium was transferred to the lower chamber of a Transwell chemotaxis plate. PBMCs were added to the upper chamber, and the plates were incubated for 3.5 hr. Then, medium was collected from the lower chamber and lymphocytes that had migrated to the lower chamber were quantified by FACS.

FIG. 5A: LNCaP-Luc/GFP cells were treated as indicated. After 24 hr, PBMC were added to the test wells (black bars), and medium was added to control wells (gray bars). Survival of LNCaP-Luc/GFP cells was measured using the Luciferase Assay System (Promega). FIG. 5B: PC3-Luc/GFP+LNCaP: LNCaP cells were treated as indicated. After 24 hr, PC3-Luc/GFPcells were added to the culture. 6 hr later, PBMCs (black bars) or medium were added to the culture (hatched bars). PC3-Luc/GFP: LNCaP growth medium was treated as indicated. After 24 hr, PC3-Luc/GFP cells were added, and 6 hr later either PBMCs (black bars) or medium (hatched bars) was added. Survival of PC3-Luc/GFP cells was measured using the Luciferase Assay System (Promega). T-test indicates high significance (* * *P≤0.001).

FIG. 6A: Spheroids of R=300-400 μm were treated as follows: (a) Untreated, (b) 400 nM dsRB-SCP, (c) 2.5 g/ml polyIC, (d) 400 nM dsRB-SCP+2.5 μg/ml polyIC. Spheroids were treated four times, on days 1, 2, 4 and 5, and then cultured for 10 additional days. Spheroid images were captured by a laser scanning confocal microscopy at the indicated times; one representative spheroid is shown per treatment. Note the prominent shedding of cells from the treated spheroid (red arrows). On Day 15, spheroids were labeled with Calcein AM (living cells; green) and Propidium Iodide (dead cells; red). Maximum areas of spheroids, measured using ImageJ, are shown in the graph (Mean and standard deviation). FIG. 6B: Upper panel: LNCaP-Luc/GFP spheroids treated as indicated. After 24 hr, $8*10^4$ PBMCs labeled with CellTracker™ Violet BMQC (Molecular Probes-Life Technologies) were added to the spheroids. Lower panel: PBMC medium without cells was added to the spheroids. Spheroids in both panels were captured by laser scanning confocal microscopy 0, 72, 96, 168 hr after treatment initiation. Living cells were detected by their GFP fluorescence. PI was added to the spheroids in the lower panel, to highlight the dead cells. PI staining of upper panel is not shown, as there is no way to distinguish between dead LNCaP-Luc/GFP cells and dead PBMCs.

BRIEF DESCRIPTION OF THE DESCRIBED SEQUENCES

Figure 1A:
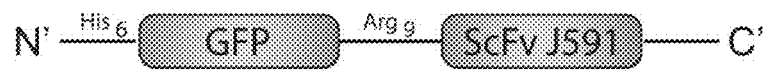
FIGS. 1A-1D: GFP-SCP binds and selectively internalizes into PSMA over-expressing cells.

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named SeqList_3152_1_2.txt created Dec. 12, 2016, about 21 KB, which is incorporated by reference herein. In the Sequence Listing:

SEQ ID NO: 1 is the amino acid sequence of the GFP-SCP protein.

SEQ ID NO: 2 is a nucleic acid sequence encoding the GFP-SCP protein.

SEQ ID NO: 3 is the amino acid sequence of the dsRB-SCP protein.

SEQ ID NO: 4 is a nucleic acid sequence encoding the dsRB-SCP protein.

SEQ ID NO: 5 is amino acid sequence of the the Arg9 linker peptide.

SEQ ID NOs 6 and 7 are forward and reverse oligonucleotide primers for IFN-β quantification.

SEQ ID NOs 8 and 9 are forward and reverse oligonucleotide primers for GAPDH quantification.

SEQ ID NO: 10 is the nucleic acid sequence of the SCP-N primer.

SEQ ID NO: 11 is the nucleic acid sequence of the SCP-C primer.

SEQ ID NO: 12 is the nucleic acid sequence of the GFP-N primer.

SEQ ID NO: 13 is the nucleic acid sequence of the GFP-C primer.

SEQ ID NO: 14 is the nucleic acid sequence of the dsRB-N primer.

SEQ ID NO: 15 is the nucleic acid sequence of the dsRB-C primer.

SEQ ID NO: 16 is the nucleic acid sequence of the 9ARG1 primer.

SEQ ID NO: 17 is the nucleic acid sequence of the 9ARG2 primer.

SEQ ID NO: 18 is the amino acid sequence of PKR dsRNA.

SEQ ID NO: 19 is the nucleic acid sequence of PKR dsRNA.

SEQ ID NO: 20 is the amino acid sequence of ScFvJ591.

SEQ ID NO: 21 is the nucleic acid sequence of ScFvJ591.

DETAILED DESCRIPTION

I. Terms

Unless otherwise noted, technical terms are used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Administration: The introduction of a composition into a subject by a chosen route. Administration of an active compound or composition can be by any route known to one of skill in the art. Administration can be local or systemic. Examples of local administration include, but are not limited to, topical administration, subcutaneous administration, intramuscular administration, intrathecal administration, In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, which release the active agents and compounds over extended time intervals for sustained treatment effects.

Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Antibody: A polypeptide ligand comprising at least a light chain or heavy chain immunoglobulin variable region, which specifically recognizes and binds an epitope of an antigen, such as PSMA. Antibodies are composed of a heavy and a light chain, each of which has a variable region, termed the variable heavy (VH) region and the variable light (VL) region. Together, the VH region and the VL region are responsible for binding the antigen recognized by the antibody. As used herein, "antibody" includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). The term also includes recombinant forms such as chimeric antibodies (for example, humanized murine antibodies), heteroconjugate antibodies (such as, bispecific antibodies).

Chimera: A nucleic acid sequence, amino acid sequence, or protein that comprises nucleic acid sequence, amino acid sequence, or protein from two or more sources, for example amino acid sequence from two or more different species. In general, chimeric sequences are the result of genetic engineering.

Expression Control Sequences: Nucleic acid sequences that regulate the expression of a heterologous nucleic acid sequence to which it is operatively linked, for example the expression of a nucleic acid encoding the chimeric recombinant proteins described herein. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons.

Functional fragments and variants of a polypeptide: Included are those fragments and variants that maintain one or more functions of the parent polypeptide. It is recognized that the gene or cDNA encoding a polypeptide can be considerably mutated without materially altering one or more the polypeptide's functions, including variants of 60%-99% sequence identity to the wildtype or parent polypeptide. First, the genetic code is well-known to be degenerate, and thus different codons encode the same amino acids. Second, even where an amino acid substitution is introduced, the mutation can be conservative and have no material impact on the essential functions of a protein. Third, part of a polypeptide chain can be deleted without impairing or eliminating all of its functions. Fourth, insertions or additions can be made in the polypeptide chain for example, adding epitope tags, without impairing or eliminating its functions. Functional fragments and variants can be of varying length. For example, some fragments have at least 10, 25, 50, 75, 100, or 200 amino acid residues. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Linker: One or more nucleotides or amino acids that serve as a spacer between two molecules, such as between two nucleic acid molecules or two peptides.

Mimetic: A mimetic is a molecule that mimics the activity of another molecule, such as a biologically active molecule. Biologically active molecules can include chemical structures that mimic the biological activities of a compound.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Subject: Living multi-cellular organisms, including vertebrate organisms, a category that includes both human and non-human mammals.

Therapeutically effective amount: A quantity of compound sufficient to achieve a desired effect in a subject being treated. An effective amount of a compound may be administered in a single dose, or in several doses, for example daily, during a course of treatment. However, the effective amount will be dependent on the compound applied, the subject being treated, the severity and type of the affliction, and the manner of administration of the compound.

II. Overview of Several Embodiments

Described herein is a chimeric recombinant protein which includes a double stranded RNA (dsRNA) binding domain; and a target binding moiety that binds to prostate surface membrane antigen (PSMA).

In particular embodiments, the chimeric recombinant protein further includes a spacer peptide between the dsRNA binding domain and the target binding moiety.

In some embodiments, dsRNA binding domain of the chimeric recombinant protein includes at least one double-stranded RNA-binding motif (dsRBM), such as a dsRBM of dsRNA dependent protein kinase (PKR), TRBP, PACT, Staufen, NFAR1, NFAR2, SPNR, RHA, or NREBP. In one example the at least one dsRBM includes a polypeptide sequence at least 70% identical to amino acids 1-197 of human PKR as set forth as SEQ ID NO: 18.

In particular embodiments of the chimeric recombinant protein, the target binding moiety is a polypeptide, antibody, antibody fragment, or antibody mimetic.

In other particular embodiments of the chimeric recombinant protein, the spacer peptide is selected from an oligopeptide comprising a protease recognition sequence; a homo-oligopeptide of a positively charged amino acids; and a combination thereof. In one example a, the spacer peptide is a homo-oligopeptide of arginine.

In a particular embodiment of the described chimeric recombinant protein, the double stranded RNA (dsRNA) binding domain is at least one dsRNA binding domain of human PKR as set forth in SEQ ID NO: 18, or a functional variant thereof, the spacer peptide is ARG9 as set forth in SEQ ID NO: 5, or a functional variant thereof, and the target binding moiety is a single chain anti-PSMA antibody as set forth in SEQ ID NO: 20, or a functional variant thereof.

In another particular embodiment, the chimeric recombinant protein includes a polypeptide at least 70% identical to the sequence set forth as SEQ ID NO: 3.

Additionally described herein is a complex which includes the described chimeric recombinant protein and dsRNA, such as a dsDNA including a polyinosinic acid strand and a polycytidylic acid strand (poly IC).

In particular embodiments, the described complexes are used in treatment of prostate cancer or inhibition of the development of tumor neovasculature, such as in methods of treatment for prostate cancer or inhibition of tumor neovasculature which include administering to a subject in need thereof a therapeutically effective amount of the described complex thereby treating the cancer or inhibiting growth of tumor neovasculature.

In some embodiments of the described methods, the complex is administered systemically or locally. In other embodiments, the methods further include administering to the subject a therapeutically effective amount of peripheral blood mononuclear cells (PBMCs).

Further described herein are nucleic acids that encode any of the described chimeric recombinant proteins.

In particular embodiments, the described nucleic acid sequences are optimized for expression in a bacterial or plant host cell.

III. Chimeric Polypeptides for Targeting dsRNA to PSMA-Expressing Cells

Described herein are chimeric recombinant polypeptides that can be used to target dsRNA to a cell expressing prostate-specific membrane antigen (PSMA). The described chimeric recombinant polypeptides include at least a dsRNA binding domain and a domain (also referred to herein as a moiety) that specifically targets PSMA. In particular embodiments, the described polypeptides also include a linker between the dsRNA binding domain and the target binding domain. Functional variants of the chimeric recombinant polypeptides are also described.

dsRNA-binding domains may readily be identified in a peptide sequence using methods available to the average person skilled in the art. The dsRNA binding domain of any one of the described recombinant proteins may include one or more double-stranded RNA-binding motif (dsRBM), such as an alpha-beta-beta-beta-alpha fold.

In certain embodiments said one or more dsRBM is selected from a dsRBM of dsRNA dependent protein kinase (PKR), TRBP, PACT, Staufen, NFAR1, NFAR2, SPNR, RHA or NREBP. In particular, the dsRNA binding domain may comprise two dsRBMs of a PKR, optionally connected by a flexible linker.

In a particular embodiment, the dsRNA binding domain is the dsRNA binding domain of human dsRNA dependent protein kinase (PKR), or a functional variant thereof, including a polypeptide that shares about 60%, 70%, 75%, 80%, 85%, 90%, 95%, or 98% sequence identity with the amino acid sequence set forth herein as SEQ ID NO: 18.

In certain embodiments, the target-binding moiety of any one of the recombinant proteins described herein includes (i) a ligand to a cell surface receptor; (ii) an antibody, such as a humanized antibody; a human antibody; a functional fragment of an antibody; a single-domain antibody, such as a Nanobody; a recombinant antibody; and a single chain variable fragment (ScFv); or (iii) an antibody mimetic, such as an affibody molecule; an affilin; an affimer; an affitin; an alphabody; an anticalin; an avimer; a DARPin; a fynomer; a Kunitz domain peptide; and a monobody, In certain embodiments, the target-binding moiety is a prostate surface membrane antigen (PSMA) ligand, such as DUPA or an analog thereof, an anti-PSMA antibody, such as an anti-PSMA scFv or a humanized or human anti-PSMA antibody (e.g. the full length antibody J591); or an anti-PSMA affibody.

In a particular embodiment, the PSMA targeting moiety is a single chain antibody against PSMA, ScFvJ591, or a functional variant thereof, including a polypeptide that shares about 60%, 70%, 75%, 80%, 85%, 90%, 95%, or 98% sequence identity with the amino acid sequence set forth herein as SEQ ID NO: 19.

The described spacer peptide can be any oligopeptide known in the art for connecting two functional domains of a polypeptide chimera. In certain embodiments, the spacer peptide (linker) includes an oligopeptide comprising a protease recognition sequence; or a homo-oligopeptide of a positively charged amino acid (at physiological pH), such as arginine.

In a particular embodiment, the linker (spacer peptide) between the dsRNA binding domain and the target binding moiety is the ARG9 peptide, or a functional variant thereof, including a polypeptide that shares about 60%, 70%, 75%, 80%, 85%, 90%, 95%, or 98% sequence identity with the amino acid sequence set forth herein as SEQ ID NO: 5.

In a particular embodiment, the chimeric recombinant polypeptide is the polypeptide having the amino acid sequence set forth herein as SEQ ID NO: 3, or a functional variant thereof, including a peptide that shares about 60%, 70%, 75%, 80%, 85%, 90%, 95%, or 98% sequence identity with SEQ ID NO: 4.

In other embodiments the variation from the described sequence can be conservative substitutions that one of skill will not expect to significantly alter the shape or charge of the polypeptide. The described polypeptides also include those polypeptides that share 100% sequence identity to those indicated, but which differ in post-translational modifications from the native or natively-produced sequence.

In particular embodiments, the described recombinant polypeptides are provided as a discrete biomolecules. In other embodiments, the described polypeptides are a domain of a larger polypeptide, such as an independently-folded structural domain, or an environment-accessible functional domain.

Additionally described herein is a complex that includes any one of the described recombinant proteins and dsRNA. In certain embodiments, the dsRNA of the complex is PKR-activating dsRNA, such as dsRNA comprising a polyinosinic acid strand and a polycytidylic acid strand (poly IC). In certain embodiments, the poly IC includes at least 22 ribonucleotides in each strand, for example, 85-300 ribonucleotides in each strand. In certain embodiments, the dsRNA of the complex comprises at least one siRNA sequence directed against a pro-oncogenic protein, such as, but not limited to, Bcl-xl, Bcl-2, Mcl-1, Stat3, Pkb/Akt.

In particular embodiments, the described complexes are a component of a pharmaceutical composition that includes a pharmaceutically acceptable carrier as described above.

Also provided herein are nucleic acids encoding the described chimeric recombinant polypeptides, such as the nucleic acid set forth herein as SEQ ID NO: 4.

It will be appreciated that due to degeneracy of the genetic code, the sequences of the described nucleic acids can vary significantly from the sequence set forth herein as SEQ ID NO 4; and without any change in the encoded polypeptide. Other and/or additional mutations in the described polypeptides, such as conservative amino acid mutations, can also be included without an appreciable difference. Accordingly, in some embodiments, the described nucleic acids share between 60%-100% sequence identity with SEQ ID NO 4, such as 60%, 70%, 75%, 80%, 85%, 90%, 95%, or 98% sequence identity. In a particular example, the nucleic acid sequence is adjusted to account for natural codon bias in a particular organism such as a bacterial or plant cell. Such adjustments are known to the art, and can be found (12)

In particular embodiments, the described nucleic acid sequences are contained within a DNA cloning and/or expression plasmid as are standard in the art. It will be appreciated that any standard expression plasmid can be used to express one or more of the described chimeric polypeptide-encoding nucleic acids. Such plasmids will minimally contain an origin of replication, selection sequence (such as, but not limited to an antibiotic resistance gene), and expression control sequences operably linked to the described nucleic acid. In particular embodiments, the expression plasmids include post-translational sequences (e.g. signal sequences to direct polypeptide processing and export) that are encoded in-frame with the described nucleic acids. In particular embodiments, the expression control sequences are those known to the art for optimized expression control in a bacterial or plant host.

Particular non-limiting examples of bacterial expression plasmids include IPTG-inducible plasmids, arabinose-inducible plasmids and the like. Other non-limiting examples of expression induction include light induction, temperature induction, nutrient-induction, and autoinduction, plant and mammalian-specific DNA expression plasmids. Custom-made expression plasmids are commercially available from suppliers such as New England Biolabs (Ipswich, Mass.) and DNA 2.0 (Menlo Park, Calif.).

In particular embodiments, the described polypeptides can be formulated for immediate release, whereby they are immediately accessible to the surrounding environment, thereby providing an effective amount of the active agent(s), upon administration to a subject, and until the administered dose is metabolized by the subject.

In yet another embodiment, the described polypeptides can be formulated in a sustained release formulation or system. In such formulations, the therapeutic agents are provided for an extended duration of time, such as 1, 2, 3, 4 or more days, including 1-72 hours, 24-48 hours, 16-36 hours, 12-24 hours, and any length of time in between. In particular embodiments, sustained release formulations are immediately available upon administration, and provide an effective dosage of the therapeutic composition, and remain available at an effective dosage over an extended period of time. In other embodiments, the sustained release formulation is not immediately available within the subject and only becomes available, providing a therapeutically effective amount of the active compound(s), after the formulation is metabolized or degraded so as to release the active compound(s) into the surrounding environment.

In one embodiment, a pump may be used. In another embodiment, the sustained released formulations include polymeric materials commonly used in the art, such as in implants, gels, capsules, and the like.

Therapeutic preparations will contain a therapeutically effective amount of at least one active ingredient, preferably in purified form, together with a suitable amount of carrier so as to provide proper administration to the patient. The formulation should suit the mode of administration.

IV. Methods of Treatment of PSMA-Associated Diseases

PSMA expression is associated with cancerous cells, particularly prostate cancer and tumor-associated neovasculature (13). In yet a further aspect, the present disclosure provides a method for treatment of cancer characterized by expression of a PSMA, said method by administering to a subject in need thereof, any one of the complexes or pharmaceutical composition described herein.

In some embodiments, the described complex is administered to the subject in combination with other pharmaceutical agents for treatment of the cancer under treatment. For example, in particular examples of cancer treatment, administration of the described can be combined with surgery, cell therapy, chemotherapy and/or radiation therapy. The one or more therapies in combination with the described polypeptides can be administered to the subject in sequence (prior to or following) or concurrently with the described polypeptides. Where applicable, in particular embodiments, combinations of active ingredients can be administered to a subject in a single or multiple formulations, and by single or multiple routes of administration. In particular embodiments, the methods of treatment include the sequential or concurrent administration of peripheral blood mononuclear cells (PBMCs).

The amount of each therapeutic agent for use in the described methods, and that will be effective, will depend on the nature of the cancer to be treated, as well its stage of the disorder or condition. Therapeutically effective amounts can be determined by standard clinical techniques. The precise dose to be employed in the formulation will also depend on the route of administration, and should be decided according to the judgment of the health care practitioner and each patient's circumstances. The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy.

The therapeutic compounds and compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. In some embodiments long-term treatment with the drug is contemplated.

The following examples are provided to illustrate certain particular features and/or embodiments. These examples should not be construed to limit the disclosure to the particular features or embodiments described.

EXAMPLES

Example 1: Methods

Cloning of GFP-SCP and dsRB-SCP

Figure 2A:
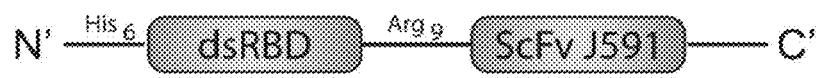
FIGS. 2A-2C: Design, expression and purification of dsRB-SCP.

Plasmids pGFP-SCP (encoding GFP linked via $Arg_9$ to the single chain antibody, ScFvJ591, against PSMA; 56 kDa) and psRB-SCP (encoding dsRB of human PKR linked via $Arg_9$ to ScFvJ591; 48 kDa) (FIG. 1A) were constructed as follows:

SCP (single chain antibody against PSMA, ScFvJ591) was amplified by PCR from plasmid SFG-Pzl (14), using primers SCP-N and SCP-C. GFP was amplified by PCR from plasmid pEGFP-N3 (Clontech), using primers GFP-N and GFP-C. dsRB was amplified by PCR from plasmid DRBM-DT-EGF (15) using primers dsRB-N and dsRB-C. To prepare the $Arg_9$ linker (GSRRRRRRRRGRKA; SEQ ID NO: 5), oligonucleotide 9ARG1 was annealed to its complementary oligonucleotide 9ARG2. The oligonucleotides used are listed in Table 1. GFP-SCP was constructed in stages in the bacterial expression vector pET28a (Novagen): GFP was cloned after the $His_6$ tag of plasmid pET28a, between the NdeI and BamHI restriction sites, SCP was cloned between the HindIII and XhoI sites, and the $Arg_9$ linker was inserted between the BamH1 and HindIII sites, to give the fusion $His_6$-GFP-$Arg_9$-SCP (FIG. 1A). For the construction of dsRB-SCP, the GFP fragment was replaced with the dsRB sequence using restriction sites NdeI and BamHI to give the fusion $His_6$-dsRB-$Arg_9$-SCP (FIG. 2A). The expected sequences were confirmed at The Center for Genomic Technologies at The Hebrew University of Jerusalem (Supplementary).

TABLE 1

Oligonucleotides used for the construction of pGFP-SCP and psRB-SCP.

| Name | Sequence 5' to 3' |
|---|---|
| SCP-N | TTTACTCGAGCGGAGGTGCAGCTGCAGC (SEQ ID NO: 10) |
| SCP-C | TTTTGCTCAGCGCCGTTACAGGTCCAGCCATG (SEQ ID NO: 11) |
| GFP-N | TTTTCATATGGTGAGCAAGGGCG (SEQ ID NO: 12) |
| GFP-C | TAAGGATCCGCCACCGCCGCTTTTCTTGTACAGC (SEQ ID NO: 13) |
| dsRB-N | TTTCATATGATGGCTGGTGATC (SEQ ID NO: 14) |
| dsRB-C | TTAGGATCCGCCACCGCCGCTCTCCGATAAGATCTGCAG (SEQ ID NO: 15) |
| 9ARG1 | GATCCCGTCGTCGCCGTCGTCGCCGTCGCGGCCGCAA (SEQ ID NO: 16) |
| 9ARG2 | AGCTTTGCGGCCGCGACGGCGACGACGGCGACGACGG (SEQ ID NO: 17) |

Expression of GFP-SCP and dsRB-SCP

The chimeric proteins were expressed in *E. coli* BL21trxB (DE3) (Novagen) which had been transformed with plasmid pRARE, which encodes tRNAs for rare codons. The bacteria were grown at 37° C., in 2×YT medium, supplemented with 25 μg/ml chloramphenicol, 30 μg/ml kanamycin, 100 μg/ml ampicillin, 1% glucose and 5% NPS buffer (1M $KH_2PO_4$, 1M $Na_2HPO_4$, 0.5M $(NH_4)_2SO_4$). When the culture reached $OD_{600}$~0.3, 0.1% glycerol and 0.1 mM L-glutamic acid were added, and the culture was moved to 42° C., to induce the expression of *E. coli* chaperones and enhance protein solubility. When the culture reached $O.D_{600}$~0.9, it was cooled down on ice and transferred to 14° C. After a 10 min adjustment period, 0.5 mmol/L IPTG was added, followed by incubation for 24 h. The bacteria were harvested and the pellet stored at −80° C. until purification.

Purification of GFP-SCP and dsRB-SCP

GFP-SCP: The pellet obtained from 1.2 L of *E. coli* BL21trxB(DE3, pRARE, pGFP-SCP) was thawed on ice in 60 ml binding buffer (Buffer A, 30 mM HEPES pH 8.3, 0.5M NaCl, 10% glycerol, 10 mM imidazole) supplemented with a protease inhibitor cocktail, 3 mg/ml lysozyme and DNase, and lysed using a LV1 microfluidizer (Microfluidics). The extract was clarified by centrifugation for 30 min (15,000×g, 4° C.), loaded onto an 8 ml nickel sepharose FF IMAC column (GE Healthcare), and washed with 10 column volumes (CV) of binding buffer, followed by 6 CV of 5% Buffer B (30 mM HEPES pH 8.3, 0.5M NaCl, 10% glycerol, 1M imidazole), 6 CV of 10% Buffer B and 1 CV of 15% Buffer B. The protein was eluted with 60% Buffer B. Fractions containing the chimera (8 ml total) were loaded on a 500 ml sephacryl S-200 gel filtration column (GE Healthcare) pre-equilibrated with GF buffer (30 mM HEPES pH 8.3, 0.5M NaCl, 10% glycerol). The fractions eluted after 0.5 CV were pooled, concentrated using Vivaspin-20 (MWCO: 30000, GE Healthcare) and loaded onto 350 ml superdex-75. The fractions eluted after 0.5 CV were subjected to SDS-PAGE and stained with InstantBlue (Expedeon). The fractions that contained highly purified chimera were pooled, concentrated using Vivaspin-20 (GE Healthcare), and stored in aliquots at −80° C.

dsRB-SCP: The pellet obtained from 6 L of *E. coli* BL21trxB(DE3, pRARE, pdsRB-SCP) was thawed in 300 ml binding buffer A supplemented with protease inhibitors, lysozyme and DNase, lysed and clarified as above. To release bound host nucleic acids, the cleared lysate was mixed 1:1 (vol:vol) with 8M urea. The mixture was incubated at 4° C. for 1.5 hr and then loaded onto 60 ml nickel sepharose FF column pre-equilibrated with buffer C (Buffer A supplemented with 0.5% Tween 80 and 4M urea), and washed with 12.4 CV Buffer C. To refold the protein, a slow linear gradient of Buffer C to Buffer D (Buffer A supplemented with 0.5% Tween 80), 10 CV, 0.8 ml/min flow was applied. The column was washed with 3 CV of 10% and 3 CV of 25% Buffer E (30 mM HEPES pH 8.3, 0.5M NaCl, 10% glycerol, 500 mM imidazole, 0.5% Tween 80), and the protein was eluted with 100% buffer E. The fractions containing the chimera were pooled and diluted 1:1 with dilution buffer (30 mM MES pH, 10% Glycerol, 0.5% Tween). The diluted protein was clarified by centrifugation for 30 min (15,000×g, 4° C.) and loaded onto a 66 ml Fracto-gel EMD SO3 IEX column (Merck). A manual step gradient (7 CV) of Buffer F (30 mM MES pH, 100 mM NaCl, 10% Glycerol, 0.001% Tween) and 25%, 27%, 30%, 37% and 38% Buffer G (30 mM HEPES pH 8.3, 2M NaCl, 10% glycerol, 0.001% Tween 80) was applied. Samples of the eluted fractions were subjected to SDS-PAGE and stained with InstantBlue (Expedeon). Fractions that contained purified chimera were pooled, concentrated, and stored at −80° C. as above.

Cell Lines

LNCaP cells were cultured in RPMI 1640 medium supplemented with 10 mM HEPES pH 7.4 and 1 mM sodium pyruvate. VCaP cells were cultured in DMEM (Dulbecco's Modified Eagle Medium). PC3 and DU145 cells were cultured in MEM (Minimum Essential Medium) supplemented with 1% non-essential amino acids, 1 mM sodium pyruvate, 10 mM Hepes pH 7.4 and 1% MEM vitamin mixture. MCF7 cells were cultured in RPMI 1640 medium. All tissue culture media were supplemented with penicillin (100 U/ml), streptomycin (100 mg/l) and 10% FBS (fetal bovine serum). All cell lines were purchased from the American Type Culture Collection (ATCC), tested and shown to be *mycoplasma*-free.

LNCaP-Luc/GFP and PC3-Luc/GFP were generated using lentiviral vectors encoding the fusion gene luciferase-GFP (Luc/GFP) as previously described (16). PBMCs were isolated from fresh human peripheral blood by standard Ficoll density-gradient centrifugation (17). All cells were incubated at 37° C. with 5% $CO_2$ in a humidified incubator. All cell culture reagents were purchased from Biological Industries, Bet Ha'emek, and Israel.

Flow Cytometry

Cells were plated onto 12-well plates at a density of $1\times10^5$ cells per well, grown for 40 hr and incubated with GFP-SCP. After incubation cells were trypsinized, washed in PBS, re-suspended in 1 ml cold PBS and subjected to flow cytometry analysis using BD FACS ARIAIII (BD Biosciences, USA) equipped with 488 nm laser. 10,000 cells were acquired for each treatment. The cells were gated to include only live cells and the subpopulation was analyzed for GFP levels. All data was analyzed using FlowJo software (Becton Dickinson).

Immunocytochemistry

LNCaP, PC3 and MCF7 cells were grown for 48 hr and incubated with 25 nM GFP-SCP for 5 hr at 37° C. After incubation cells were fixed with 4% Paraformaldehyde, washed twice with PBS, permeabilized and stained with goat anti-GFP antibody (1:1000, Abcam ab5450), followed by incubation with DyLight 488-conjugated anti-goat secondary antibody (1:300, Jackson ImmunoResearch Laboratories). 4, 6-diamidino-2-phenylindole (DAPI) was used to stain DNA. Stained samples were observed with a confocal microscope (FLUOVIEW FV-1000, Olympus, Japan).

Live Cell Imaging

GFP-SCP localization was observed in live LNCaP cells, using time-lapse confocal microscopy (FLUOVIEW FV-1000, Olympus, Japan). LNCaP cells were grown for 48 hr in 8-well μ-slides (Ibidi, cat no 80826). After changing the medium, 200 nM GFP-SCP was added directly to the chamber, the cells were immediately observed and subsequent images were taken every 6 minutes, for 72 mins. The images were analyzed using FLUOVIEW Viewer software (Ver.4.2).

dsRNA Electrophoretic Mobility Shift Assay (EMSA)

500 bp long dsRNA transcribed from the control template of the MEGAscript® RNAi Kit (AM1626) was labeled using the Label IT® Nucleic Acid Labeling Reagents kit (Mirus). 1 μg of labeled dsRNA was incubated for 30 minutes with increasing amounts of purified dsRB-SCP (0.5-3 μg), and the mixture was electrophoresed on a 2% agarose gel. The gel was visualized by staining with ethidium bromide.

Preparation of dsRB-SCP/polyIC Complex

PolyIC used for all experiments was low molecular weight (LMW) polyIC (InvivoGen). For all experiments, dsRB-SCP/polyIC, polyIC alone or dsRB-SCP alone was prepared in binding buffer (30 mM HEPES pH 8.3, 0.5M NaCl, 10% glycerol) at the concentrations indicated in the text, and pre-incubated for 45 minutes at room temperature, before addition to the cells.

Survival Assay

LNCaP, VCaP, PC3 and MCF7 cells were seeded in 96-well plates in triplicate (5000 cells/well) and grown overnight. dsRB-SCP/polyIC, polyIC alone or dsRB-SCP was added to the cells, which were then incubated for additional 100 hr. Survival was measured using the CellTiter-Glo Luminescent Cell Viability Assay (Promega).

For the rescue experiment, LNCaP cells were seeded (5000 cells/well) in three 96-well plates pre-coated with poly-lysine. For each plate, treatments were repeated in triplicate wells and the cells were grown overnight. The cells were then treated with dsRB-SCP/polyIC, polyIC alone or dsRB-SCP alone. The first plate was assayed for survival after 100 hr. The medium in the second plate was changed after 100 hr and survival was assayed after 172 hr. The medium in the third plate was changed after 100 hr and again after 172 hr and survival was assayed after 344 hr.

Immunoblots

LNCaP cells were seeded in 6-well plates ($1\times10^6$ cells/well), grown overnight and treated with dsRB-SCP/polyIC or polyIC alone at the indicated concentrations. After 7, 16 or 24 hr cells were lysed with boiling Laemmli sample buffer (10% glycerol, 50 mmol/L Tris-HCl, pH 6.8, 3% SDS, and 5% 2-mercaptoethanol) and the lysates were then subjected to western blot analysis (18). The cleavage of PARP and caspase-3 was monitored using anti-PARP (cat #95425), anti-caspase3 (cat #96625) and anti-cleaved caspase-3 (cat #96615) (all from Cell Signaling Technology). As an internal control to normalize the amount of protein applied in each lane the blots were also incubated with anti-GAPDH (Santa Cruz, sc-25778).

Detection of Secreted Chemokines (IP-10 and RANTES) by ELISA

LNCaP cells were seeded in 96-well plates in triplicate and grown overnight (10,000 cells/well). Cells were then treated with dsRB-SCP/polyIC or polyIC alone at the indicated concentrations. After 48 hr the medium was collected and the concentrations of IP-10 and RANTES were measured using commercial ELISA kits (PeproTech).

RNA Isolation, cDNA Synthesis and Quantitative Real-Time PCR

LNCaP cells were seeded in 24-well plates (500,000 cells per well) and grown overnight. Cells were then treated for 4 hr with dsRB-SCP/polyIC, polyIC alone or dsRB-SCP alone at the indicated concentrations. The cells were lysed and total RNA was extracted using the EZ-10 DNA Away RNA-Miniprep Kit (Bio Basic). Complementary DNA (cDNA) was synthesized using the High Capacity cDNA Reverse Transcription Kit (Applied Biosystems). IFN-β gene expression levels were compared using quantitative real-time PCR and normalized to GAPDH expression using the ΔΔ CT method. The primers used for IFN-β quantification were: forward: 5' ATGACCAACAAGTGTCTCCTCC 3' (SEQ ID NO: 6) and reverse: 5' GCTCATG-GAAAGAGCTGTAGTG 3' (SEQ ID NO: 7). The primers for GAPDH quantification were forward: 5' GAGCCA-CATCGCTCAGAC 3' (SEQ ID NO: 8) and reverse: 5' CTTCTCATGGTTCACACCC 3' (SEQ ID NO: 9).

Chemotaxis of PBMC

LNCaP cells were seeded in 24-well plates pre-coated with poly-lysine (250,000 cells/well) and grown overnight. Then, the medium was replaced by low-serum medium (0.15% FBS) and the cells were treated with dsRB-SCP/polyIC at the indicated concentrations. After 48 hr conditioned medium was collected from the cells and placed in the bottom well of a 24-well Transwell system (microporous polycarbonate membrane (0.5 m) Corning; Costar). Freshly isolated PBMCs ($1\times10^6$) in low-serum medium (0.15% FBS) were added to the upper chamber. After 3.5 hr, medium from the lower chamber was collected and the migrated cells were quantified by FACS analysis, scatter-gating on lymphocytes.

Analysis of Bystander Effects in Co-Culture Systems

In order to measure the viability of a single cell line in co-culture with other cells, we generated cells that expressed luciferase (either LNCaP-Luc/GFP or PC3-Luc/GFP).

The immune-cell-mediated bystander effect was analyzed using LNCaP-Luc/GFP cells co-cultured with PBMCs: LNCaP-Luc/GFP cells were seeded in triplicate in 96-well plates pre-coated with poly-lysine (10,000 cells/well) and grown overnight. The cells were then treated with dsRB-SCP/polyIC, polyIC alone or dsRB-SCP alone at the indicated concentrations. After 24 hr, freshly isolated PBMCs were added to the culture ($1\times10^5$ per well). 48 hr later, the survival of LNCaP-Luc/GFP cells was measured based on luciferase activity using the Luciferase Assay System (Promega).

The combined direct and immune-cell-mediated bystander effect was analyzed using LNCaP cells co-cultured with PC3-Luc/GFP and PBMCs: LNCaP cells were seeded in triplicate in 96-well plates pre-coated with poly-lysine (6,000 cells/well) and grown overnight, and the cells were treated with dsRB-SCP/polyIC, polyIC alone or dsRB-SCP alone. After 16 hr PC3-Luc/GFP cells (4,000 cells/well) were added to the culture. 24 hr after treatment freshly isolated PBMCs ($1\times10^5$/well) were added to the culture. 48 hr later survival of the PC3-Luc/GFP cells was measured based on luciferase activity, using the Luciferase Assay system (Promega).

Tumor Spheroid Model

Tumor spheroids were generated using agar-coated plates. 96-well plates were coated with 50 μl/well agar (1.5% (wt/vol) dissolved in RPMI) according to ref (19). LNCaP or LNCaP-Luc/GFP cells were seeded (2000 cells per well) and incubated. After 97 hr, a single spherical spheroid of R=300-400 μm had formed in each well.

To measure LNCaP spheroids following treatment with dsRB-SCP/polyIC, we transferred the spheroids individually to 96-well plate (1 spheroid/well) pre-coated with a very thin, even layer of polyHEMA (120 mg/ml dissolved in 95% ethanol). To transfer the spheroids, we first lifted each spheroid together with its 200 μl of medium into a 96U-well plate (with U-shaped wells). The plate was centrifuged for 10 minutes at 220 g and the medium was replaced with 80 μl of fresh medium. The spheroid was then transferred, together with its 80 μl of medium, to the polyHEMA-coated plate. dsRB-SCP/polyIC, polyIC alone or dsRB-SCP alone were added at the indicated concentrations. Treatment continued for 5 days. On days 1, 2, 4 and 5, half of the medium in each well was removed and replaced with fresh medium containing the appropriate treatment. On Day 15, spheroids were stained with calcein AM (1:1000, Molecular Probes c3099) and 0.5 μg/ml propidium iodide. Spheroids were monitored using confocal microscopy and size was measured using ImageJ software.

To analyze the immune-cell-mediated bystander effects on tumor spheroids, we treated LNCaP-Luc/GFP spheroids once, directly on the agar plate, with dsRB-SCP/polyIC, polyIC alone or dsRB-SCP alone at the indicated concentrations. After 24 hr fresh PBMCs were labeled using 1 μM CellTracker™ Violet BMQC (Molecular Probes—Life Technologies) according to the manufacturer's protocol. $8\times10^4$ PBMCs were added to the spheroid culture. The co-culture was monitored using confocal microscopy.

Example 2: Construction and Assay of PSMA-Targeting Chimeric Proteins

ScFvJ591 Selectively Targets PSMA Over-Expressing Prostate Cancer Cells and Efficiently Delivers its Cargo into the Cells We first tested whether the single chain antibody ScFvJ591 could be used as a homing ligand, as part of a chimeric protein. We generated pGFP-Arg$_9$-ScFvJ591, encoding GFP as a tracking marker fused to the single chain antibody against PSMA, ScFvJ591, via a linker comprising an endosomal escape sequence (FIG. 1A). The 56 kDa recombinant protein, GFP-SCP (GFP-Arg$_9$-ScFvJ591), was expressed in E. coli and purified in a 3-step purification process comprising affinity purification followed by two steps of gel filtration (see Methods).

Figure 1B:
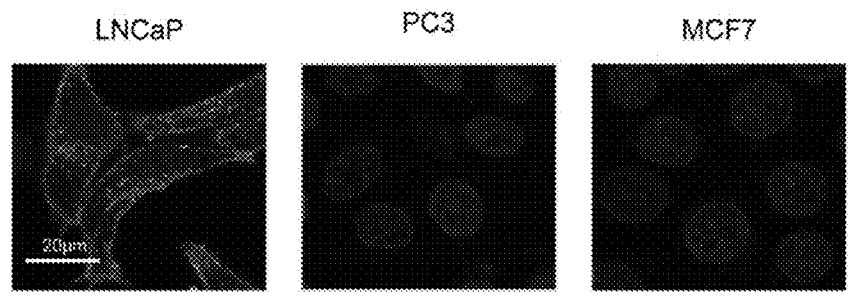
Figure 1C:
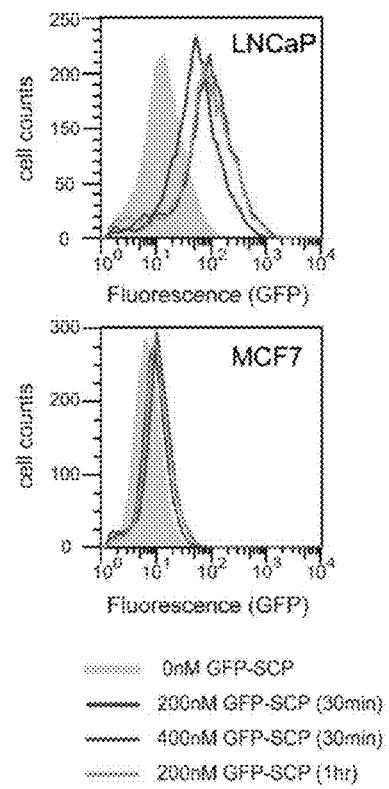
Figure 1D:
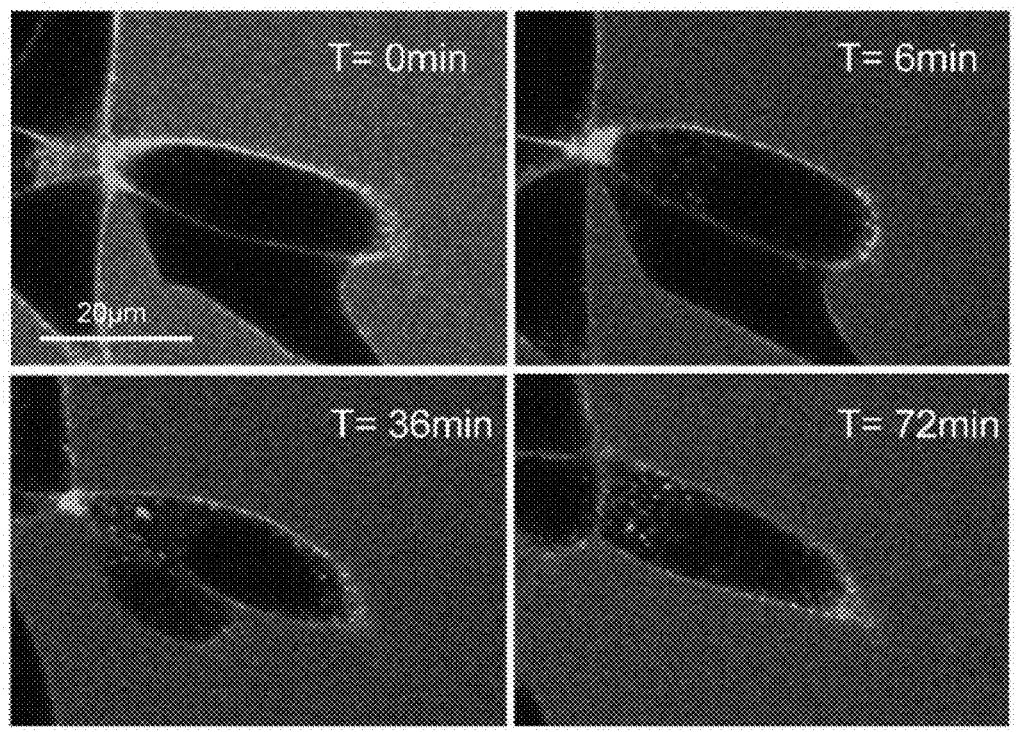

We tested the selectivity of GFP-SCP using confocal microscopy. We incubated the chimeric protein with LNCaP cells, which over express PSMA, and analyzed binding after 5 hr. PC3 and MCF7 cells, which do not express PSMA, served as negative controls. The confocal images demonstrated that GFP-SCP bound to LNCaP cells and was selectively internalized, while no binding was evident in PC3 or MCF7 cells (FIG. 1B). We next compared uptake of GFP-SCP to LNCaP and MCF7 cells using flow cytometry. We used two doses of GFP-SCP (200 nM, 400 nM) over two time periods (30 min, 60 min). The accumulation of GFP- SCP was measured by the resulting fluorescence shift. As expected, the observed fluorescence levels were correlated with the concentration of GFP-SCP and incubation period (FIG. 1C). These results suggest time-dependent and dose-dependent internalization of GFP-SCP. In contrast, in MCF7 cells, which lack PSMA, no accumulation of GFP-SCP was observed (FIG. 1C). To monitor the localization of GFP-SCP, we incubated LNCaP cells with GFP-SCP and observed them using live-cell confocal microscopy. Initially, GFP-SCP fluorescence was confined to the cell surface and no free diffusion was observed (FIG. 1D). Minutes later, GFP-SCP entered the cell via endocytosis, as indicated by the appearance of small intracellular punctate structures (FIG. 1D). Over time, these structures increased in number. In addition, increased intracellular diffused powdery fluorescence was observed (FIG. 1D), indicating that the GFP had escaped from the endosome and diffused to the cytosol. The accumulation of the GFP inside the cell increased linearly over the first 40 min after binding (FIG. 1D).

Figure 2B:
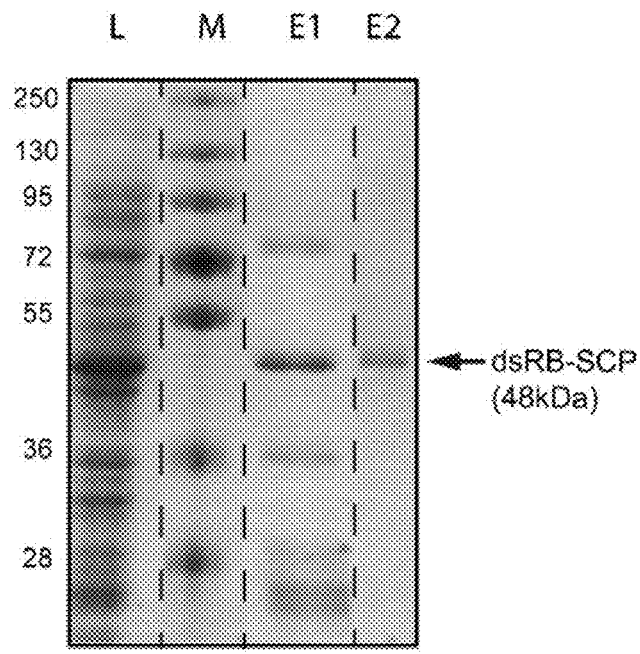
Figure 2C:
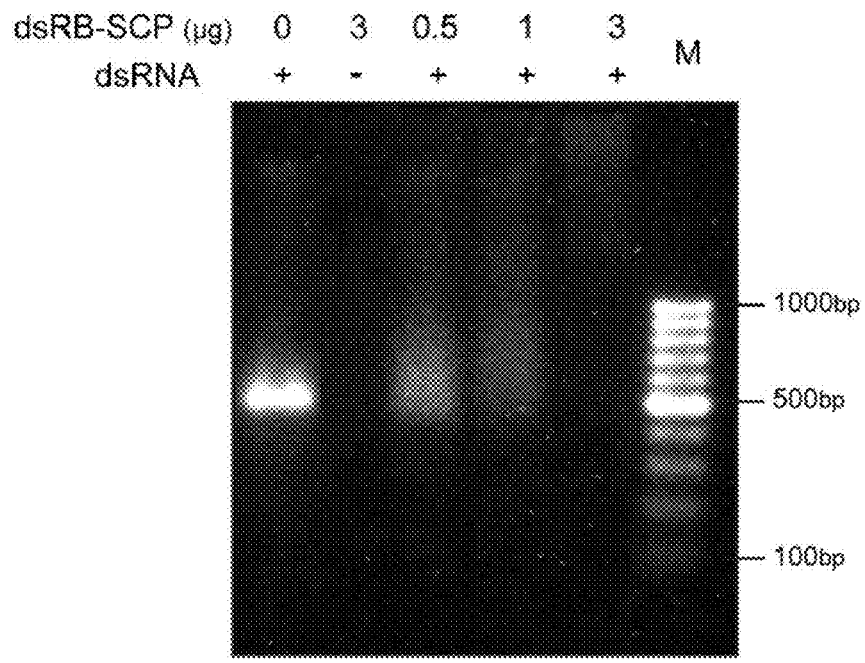
Figure 3A:
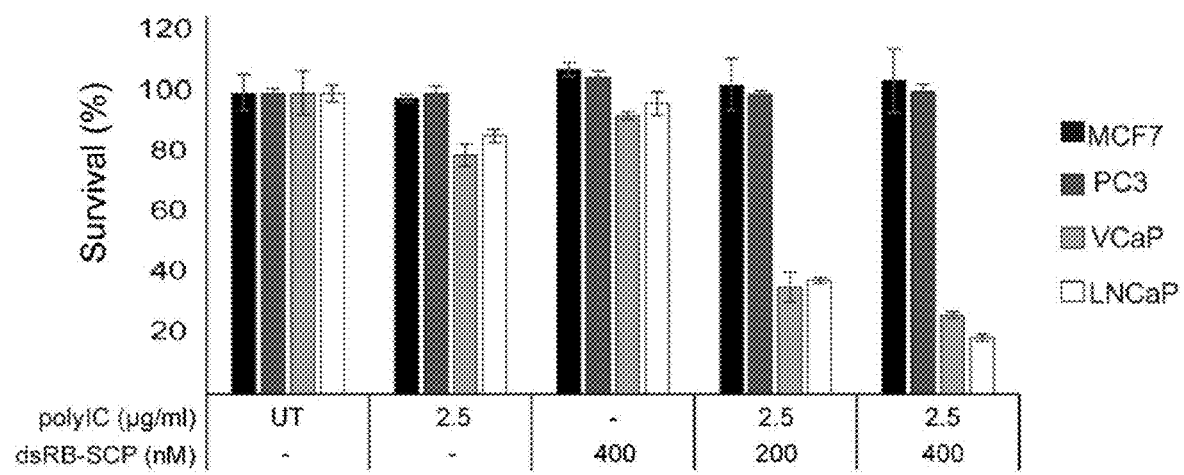
FIGS. 3A-3C: dsRB-SCP/polyIC selectively induces apoptosis of PSMA over-expressing cells.
Figure 3B:
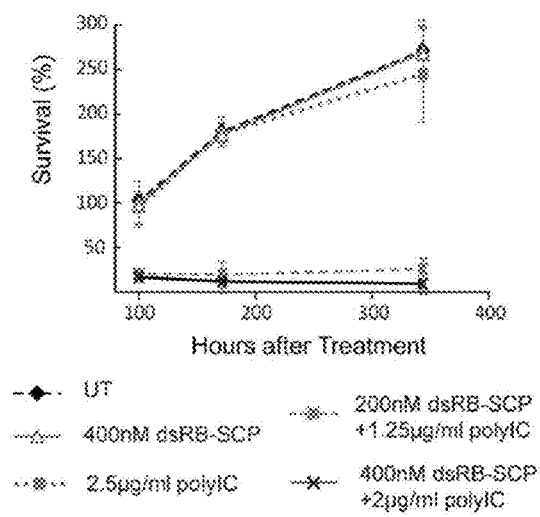
Figure 3C:
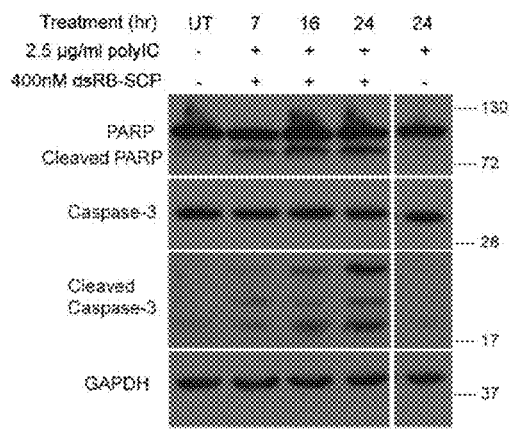
Figure 4A:
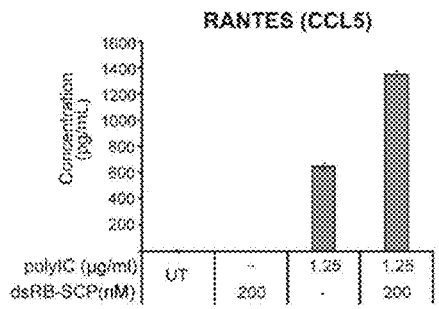
FIGS. 4A-4D: dsRB-SCP/polyIC leads to secretion of pro-inflammatory cytokines and recruitment of PBMCs.
Figure 4B:
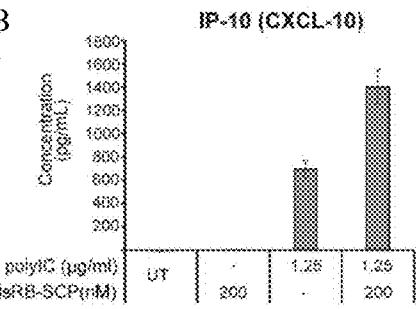
Figure 4C:
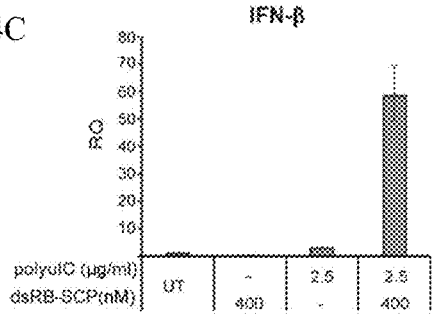

Design, Expression and Purification of a Chimeric Protein that can Carry and Internalize polyIC Selectively into PSMA Over-Expressing Prostate Cancer Cells Based on the structure of the GFP-SCP chimera, we designed a chimeric protein that would specifically deliver polyIC into PSMA over-expressing cells. We replaced the GFP moiety with the dsRNA-binding domains of PKR (dsRBDs) (FIG. 2A). The chimeric 48 kDa protein, dsRB-SCP (dsRB-9Arg-ScFvJ591), was expressed in *E. coli*. and purified using unfolding and refolding steps (FIG. 2B) as described in Example 1. The binding of the purified protein to dsRNA was evaluated. dsRB-SCP was incubated with dsRNA of defined length (500 bp) and the mixture was electrophoresed on an agarose gel (FIG. 2C). The naked dsRNA control ran at the expected position in the gel (FIG. 2C). The electrophoresis of dsRNA that had been incubated with dsRB-SCP was retarded in a dose-dependent manner (FIG. 2C), confirming that the chimeric protein bound the dsRNA.

dsRB-SCP Complexed with polyIC Selectively Kills PSMA Over-Expressing Cells by Inducing Apoptosis We evaluated the killing effect of the dsRB-SCP/polyIC complex using four cell lines: LNCaP and VCaP, which over-express PSMA, and MCF7 and PC3, which do not express PSMA. dsRB-SCP selectively delivered polyIC into the PSMA-over-expressing cells (LNCaP and VCaP), killing up to 80% of the cells (FIG. 3A). Cells which do not express PSMA (MCF7 and PC3), were not killed by the treatment (FIG. 3A). The remaining 20% of LNCaP cells were deemed permanently arrested, as no regrowth was observed 250 hr after washing out the chimera (350 hr after treatment) (FIG. 3B). dsRB-SCP/polyIC induced cell death by activating apoptotic pathways, as indicated by the cleavage of caspase-3 and PARP (FIG. 3C). In cells treated with polyIC alone no cleavage of caspase-3 or of PARP was detected (FIG. 3C). dsRB-SCP/polyIC treatment induces cytokine secretion and chemotaxis of immune cells The presence of dsRNA inside the cell activates the production of anti-proliferative and pro-apoptotic cytokines and chemokines (20). To determine whether dsRB-SCP/polyIC can trigger similar effects we analyzed the production of three main cytokines in the cell: IP-10 and RANTES, both involved in the chemo-attraction of immune cells and IFN-β, which plays a key role in the differentiation of immune cells (21). The secretion of IP-10 and RANTES into the medium, as measured by ELISA, was partially induced by polyIC alone, as reported previously (22). Treatment with dsRB-SCP/polyIC led to a further 2-fold increase in IP-10 and RANTES secretion (FIG. 4A-B). IFN-β expression was not affected by polyIC or dsRB-SCP alone, but treatment with dsRB-SCP/polyIC led to very strong induction of IFN-β expression, as measured by qRT-PCR (FIG. 4C).

Figure 4D:
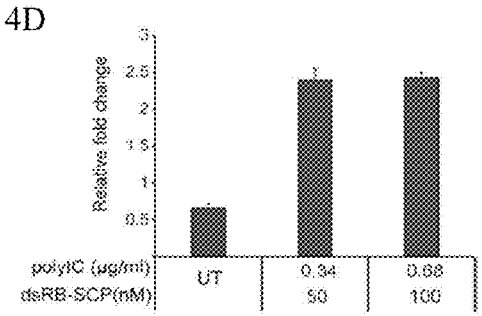

To study whether the secreted cytokines attract immune cells, we examined whether the medium from dsRB-SCP/polyIC-treated LNCaP cells induced the chemotaxis of freshly isolated PBMCs. FIG. 4D shows that an increased number of PBMCs migrated towards conditioned medium from cells that were treated with dsRB-SCP/polyIC compared to medium from untreated cells.

Bystander Effects Induced by dsRB-SCP/polyIC

Figure 5A:
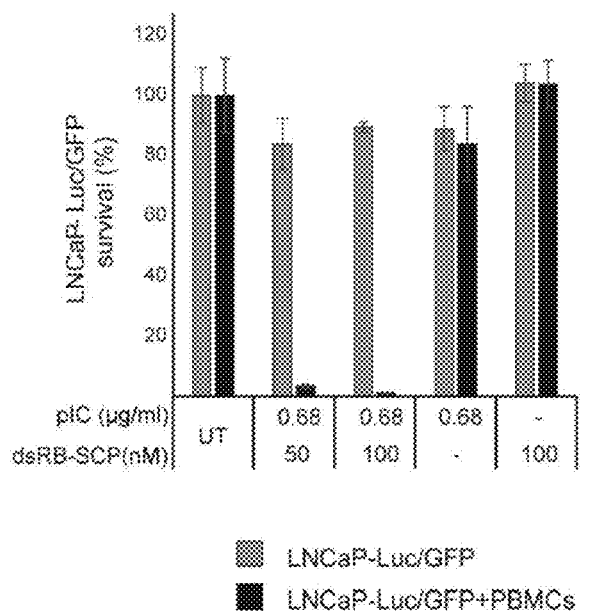
FIGS. 5A-5B: dsRB-SCP/polyIC induces direct and PBMC-mediated bystander effects.

We next tested whether the recruited immune cells could evoke an immune-cell-mediated bystander effect. We treated LNCaP-Luc/GFP cells, which stably express luciferase, with a low dose of dsRB-SCP/polyIC, followed by co-incubation with PBMCs. We used luciferase activity as a measure for the survival of the LNCaP-Luc/GFP cells. Results showed eradication of the LNCaP-Luc/GFP cells (FIG. 5A). In contrast, in the absence of PBMCs, luciferase level was barely affected. These results suggest that dsRB-SCP/polyIC induces a powerful immune-cell-mediated bystander effect.

Figure 5B:
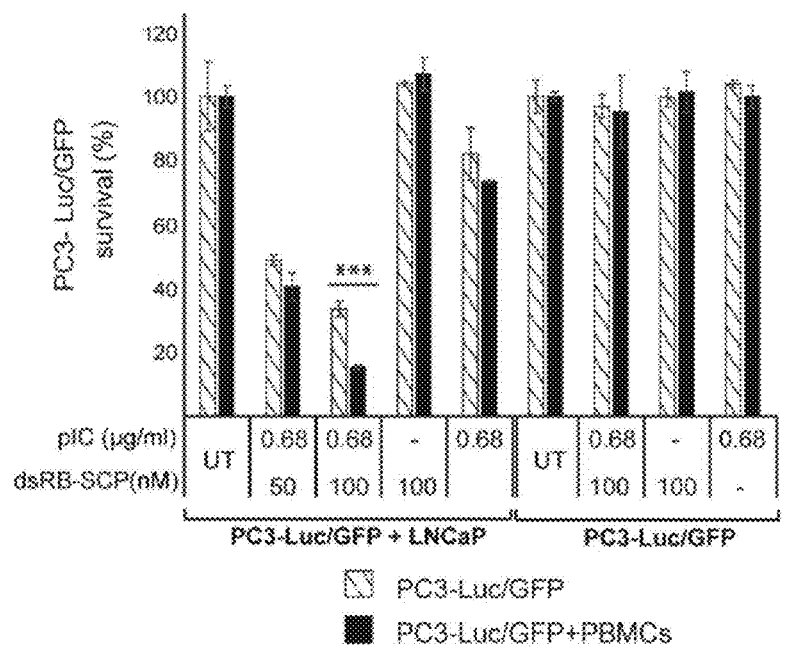

To evaluate whether dsRB-SCP/polyIC also induces a direct bystander effect, LNCaP cells were co-incubated with PC3-Luc/GFP cells, which do not express PSMA. dsRB-SCP/polyIC treatment resulted in the killing of up to 60% of the PC3-Luc/GFP cells (FIG. 5B). Since PC3-Luc/GFP cells are not targeted by dsRB-SCP/polyIC (FIG. 5B), we infer that the death of these cells is a result of a direct bystander effect elicited by the dsRB-SCP/polyIC-targeted LNCaP cells. Addition of human PBMCs to this co-culture system led to a significant increase in the killing rate of the PC3-Luc/GFP cells (FIG. 5B), indicating the additional involvement of an immune-cell-mediated bystander effect under these conditions.

dsRB-SCP/polyIC Destroys Tumor Spheroids

Figure 6A:
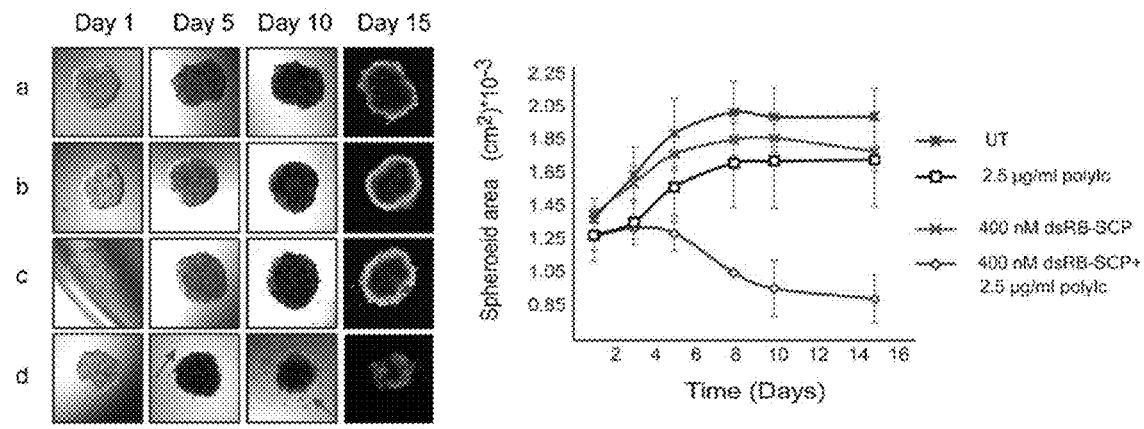
FIGS. 6A-6B: dsRB-SCP/polyIC treatment together with PBMCs leads to the destruction of LNCaP spheroids.

We next evaluated the efficacy of dsRB-SCP/polyIC in a 3D tumor spheroid model. In vitro 3D models closely resemble the architecture of human tumors (23) and feature high-resistance to anti-cancer drugs (24). LNCaP spheroids were generated and allowed to reach a diameter of 300-400 μm. The spheroids were then transferred to a polyHEMA plate and treated repeatedly with dsRB-SCP/polyIC (400 nM dsRB-SCP, 2.5 μg/ml polyIC) over the course of 5 days. By day 5, the spheroids that were treated with dsRB-SCP/polyIC began to shrink and shed dead cells, while the untreated spheroids increased in size (FIG. 6A). On day 15, the spheroids were stained with calcein AM and propidium iodide to monitor viability (FIG. 6A). The dsRB-SCP/polyIC-treated spheroids demonstrated significant structural damage and contained large numbers of dead cells (FIG. 6A). In contrast, the untreated spheroids and spheroids treated with only polyIC or only dsRB-SCP, maintained a typical intact structure (11), where the cells at the surface were alive and the cells at the core were necrotic (FIG. 6A).

Figure 6B:
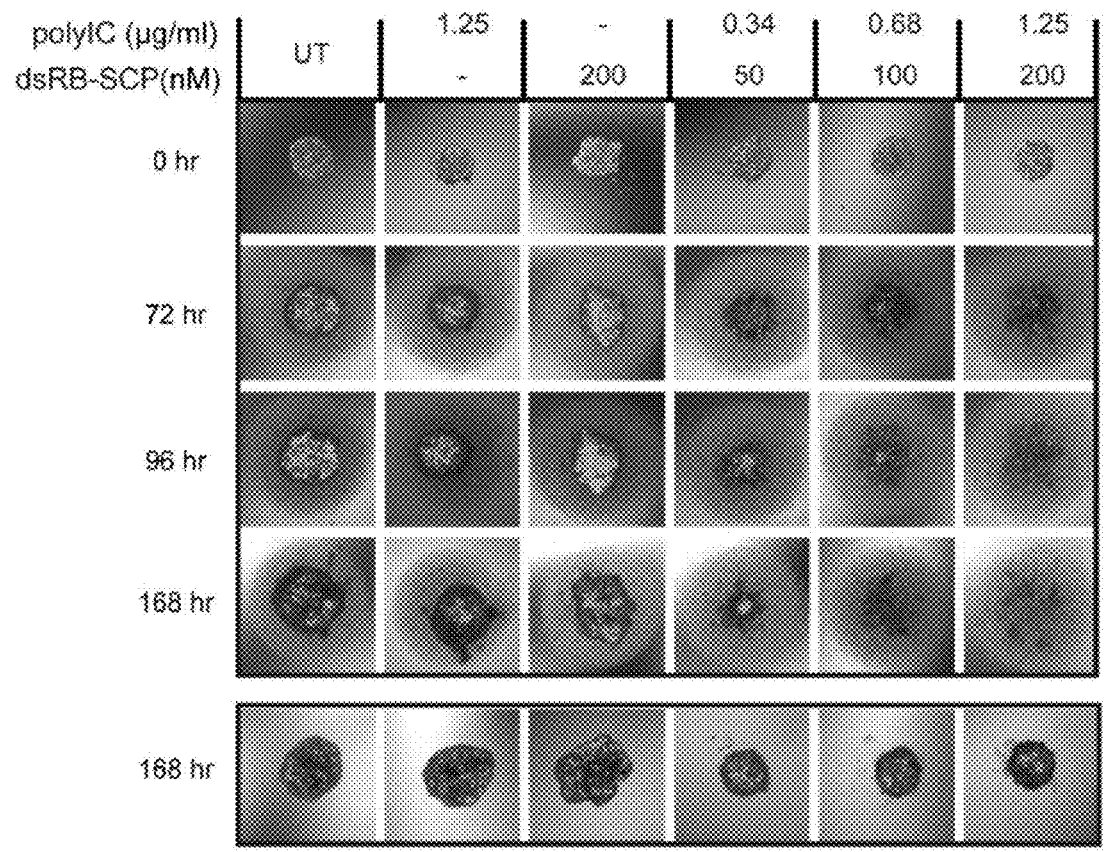

To more closely mimic in vivo conditions and test the immune-cell-mediated bystander effect on the spheroids, we added PBMCs to treated spheroids. LNCaP-Luc/GFP spheroids were treated once with dsRB-SCP/polyIC, and 24 hr later freshly isolated PBMCs were added to the culture. Even at the lowest dose of dsRB-SCP/polyIC, spheroid disassembly was already evident 72 hr after the initiation of the treatment or 48 hr after PBMCs addition (FIG. 6B). At higher doses, complete spheroid destruction was observed 96 hr after the initiation of the treatment. After additional 72 hr, only dead cells were evident with no GFP fluorescence (FIG. 6B). As a control, the same treatment was performed in absence of PBMCs. At the end point (168 hr), the treatment resulted in visible cell death and disassembly of the spheroid (FIG. 6B lower panel) but the effect was weaker compared to the levels observed in the presence of PBMCs. Thus, dsRB-SCP/polyIC has a potent effect on spheroids, and this effect is greatly magnified by the addition of immune cells.

REFERENCES

1. Luo, J., Beer, T. M., and Graff, J. N. (2016) Treatment of Nonmetastatic Castration-Resistant Prostate Cancer, *Oncology* (Williston Park) 30, 336-344,
2. Attard, G., Sarker, D., Reid, A., Molife, R., Parker, C., and de Bono, J. S. (2006) Improving the outcome of patients with castration-resistant prostate cancer through rational drug development, *British journal of cancer* 95, 767-774, 10.1038/sj.bjc.6603223
3. Javidan, J., Deitch, A. D., Shi, X. B., and de Vere White, R. W. (2005) The androgen receptor and mechanisms for androgen independence in prostate cancer, *Cancer investigation* 23, 520-528, 10.1080/07357900500202721
4. Akhtar, N. H., Pail, O., Saran, A., Tyrell, L., and Tagawa, S. T. (2012) Prostate-specific membrane antigen-based therapeutics, *Advances in urology* 2012, 973820, 10.1155/2012/973820
5. Sweat, S. D., Pacelli, A., Murphy, G. P., and Bostwick, D. G. (1998) Prostate-specific membrane antigen expression is greatest in prostate adenocarcinoma and lymph node metastases, *Urology* 52, 637-640,
6. Wright, G. L., Jr., Grob, B. M., Haley, C., Grossman, K., Newhall, K., Petrylak, D., Troyer, J., Konchuba, A., Schellhammer, P. F., and Moriarty, R. (1996) Upregulation of prostate-specific membrane antigen after androgen-deprivation therapy, *Urology* 48, 326-334,
7. Mannweiler, S., Amersdorfer, P., Trajanoski, S., Terrett, J. A., King, D., and Mehes, G. (2009) Heterogeneity of prostate-specific membrane antigen (PSMA) expression in prostate carcinoma with distant metastasis, *Pathology oncology research: POR* 15, 167-172, 10.1007/s12253-008-9104-2
8. Tagawa, S. T., Milowsky, M. I., Morris, M., Vallabhajosula, S., Christos, P., Akhtar, N. H., Osborne, J., Goldsmith, S. J., Larson, S., Taskar, N. P., Scher, H. I., Bander, N. H., and Nanus, D. M. (2013) Phase II study of Lutetium-177-labeled anti-prostate-specific membrane antigen monoclonal antibody J591 for metastatic castration-resistant prostate cancer, *Clinical cancer research: an official journal of the American Association for Cancer Research* 19, 5182-5191, 10.1158/1078-0432.CCR-13-0231
9. Galsky, M. D., Eisenberger, M., Moore-Cooper, S., Kelly, W. K., Slovin, S. F., DeLaCruz, A., Lee, Y., Webb, I. J., and Scher, H. I. (2008) Phase I trial of the prostate-specific membrane antigen-directed immunoconjugate MLN2704 in patients with progressive metastatic castration-resistant prostate cancer, *Journal of clinical oncology: official journal of the American Society of Clinical Oncology* 26, 2147-2154, 10.1200/JCO.2007.15.0532
10. van Leeuwen, P. J., Stricker, P., Hruby, G., Kneebone, A., Ting, F., Thompson, B., Nguyen, Q., Ho, B., and Emmett, L. (2016) (68) Ga-PSMA has a high detection rate of prostate cancer recurrence outside the prostatic fossa in patients being considered for salvage radiation treatment, *BJU international* 117, 732-739, 10.1111/bju.13397
11. Phung, Y. T., Barbone, D., Broaddus, V. C., and Ho, M. (2011) Rapid generation of in vitro multicellular spheroids for the study of monoclonal antibody therapy, *Journal of Cancer* 2, 507-514,
12. Puigbo, P., Guzman, E., Romeu, A., and Garcia-Vallve, S. (2007) OPTIMIZER: a web server for optimizing the codon usage of DNA sequences, *Nucleic acids research* 35, W126-131, 10.1093/nar/gkm219
13. Rajasekaran, A. K., Anilkumar, G., and Christiansen, J. J. (2005) Is prostate-specific membrane antigen a multifunctional protein? *American journal of physiology. Cell physiology* 288, C975-981, 10.1152/aj pcell.00506.2004
14. Gong, M. C., Latouche, J. B., Krause, A., Heston, W. D., Bander, N. H., and Sadelain, M. (1999) Cancer patient T cells genetically targeted to prostate-specific membrane antigen specifically lyse prostate cancer cells and release cytokines in response to prostate-specific membrane antigen, *Neoplasia* 1, 123-127,
15. Edinger, N., Lebendiker, M., Klein, S., Zigler, M., Langut, Y., and Levitzki, A. (2016) Targeting polyIC to EGFR over-expressing cells using a dsRNA binding protein domain tethered to EGF, *PloS one* 11, e0162321, 10.1371/journal.pone.0162321
16. Zigler, M., Shir, A., Joubran, S., Sagalov, A., Klein, S., Edinger, N., Lau, J., Yu, S. F., Mizraji, G., Globerson Levin, A., Sliwkowski, M. X., and Levitzki, A. (2016) HER2-Targeted Polyinosine/Polycytosine Therapy Inhibits Tumor Growth and Modulates the Tumor Immune Microenvironment, *Cancer immunology research* 10.1158/2326-6066.CIR-15-0203
17. Shir, A., Ogris, M., Roedl, W., Wagner, E., and Levitzki, A. (2011) EGFR-homing dsRNA activates cancer-targeted immune response and eliminates disseminated EGFR-overexpressing tumors in mice, *Clinical cancer research: an official journal of the American Association for Cancer Research* 17, 1033-1043, 10.1158/1078-0432.CCR-10-1140
18. Mizrachy-Schwartz, S., Cohen, N., Klein, S., Kravchenko-Balasha, N., and Levitzki, A. (2011) Upregulation of AMP-activated protein kinase in cancer cell lines is mediated through c-Src activation, *The Journal of biological chemistry* 286, 15268-15277, 10.1074/jbc.M110.211813
19. Friedrich, J., Seidel, C., Ebner, R., and Kunz-Schughart, L. A. (2009) Spheroid-based drug screen: considerations and practical approach, *Nature protocols* 4, 309-324, 10.1038/nprot.2008.226
20. Der, S. D., and Lau, A. S. (1995) Involvement of the double-stranded-RNA-dependent kinase PKR in interferon expression and interferon-mediated antiviral activity, *Proceedings of the National Academy of Sciences of the United States of America* 92, 8841-8845,
21. Kumar, A., Zhang, J., and Yu, F. S. (2006) Toll-like receptor 3 agonist poly(I:C)-induced antiviral response in human corneal epithelial cells, *Immunology* 117, 11-21, 10.1111/j.1365-2567.2005.02258.x
22. Galli, R., Starace, D., Busa, R., Angelini, D. F., Paone, A., De Cesaris, P., Filippini, A., Sette, C., Battistini, L., Ziparo, E., and Riccioli, A. (2010) TLR stimulation of prostate tumor cells induces chemokine-mediated recruitment of specific immune cell types, *J Immunol* 184, 6658-6669, 10.4049/jimmunol.0902401
23. Kim, J. B. (2005) Three-dimensional tissue culture models in cancer biology, *Seminars in cancer biology* 15, 365-377, 10.1016/j.semcancer.2005.05.002
24. Takagi, A., Watanabe, M., Ishii, Y., Morita, J., Hirokawa, Y., Matsuzaki, T., and Shiraishi, T. (2007) Three-dimensional cellular spheroid formation provides human prostate tumor cells with tissue-like features, *Anticancer research* 27, 45-53, In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A chimeric recombinant protein comprising: a double stranded RNA (dsRNA) binding domain; and a target binding moiety that binds to prostate surface membrane antigen (PSMA), and further comprising a spacer peptide between the dsRNA binding domain and the target binding moiety, wherein the spacer peptide is ARG9 as set forth in SEQ ID NO: 5, wherein the target binding moiety is an antibody or antigen-binding fragment of an antibody.

2. The chimeric recombinant protein of claim 1, wherein the dsRNA binding domain comprises at least one double-stranded RNA-binding motif (dsRBM).

3. The chimeric recombinant protein of claim 2, wherein the at least one dsRBM is selected from a dsRBM of dsRNA dependent protein kinase (PKR), TRBP, PACT, Staufen, NFAR1, NFAR2, SPNR, RHA, and NREBP.

4. The chimeric recombinant protein of claim 2, wherein the at least one dsRBM comprises a polypeptide sequence identical to amino acids 1-169 of human PKR as set forth as SEQ ID NO: 18.

5. The chimeric recombinant protein of claim 1, wherein the double stranded RNA (dsRNA) binding domain is at least one dsRNA binding domain of human PKR as set forth in SEQ ID NO: 18, and wherein the target binding moiety is a single chain anti-PSMA antibody as set forth in SEQ ID NO: 20.

6. The chimeric recombinant protein of claim 5, comprising a polypeptide identical to the sequence set forth as SEQ ID NO: 3.

7. A complex comprising the chimeric recombinant protein of claim 1 and dsRNA.

8. The complex of claim 7, wherein the dsRNA comprises a polyinosinic acid strand and a polycytidylic acid strand (poly IC).

9. A nucleic acid comprising a nucleic acid sequence encoding the recombinant protein of claim 1.

10. The nucleic acid of claim 9, wherein the nucleic acid sequence is optimized for expression in a bacterial or plant host cell.

11. The complex of claim 7, wherein the dsRNA binding domain comprises at least one double-stranded RNA-binding motif (dsRBM).

12. The complex of claim 11, wherein the dsRNA comprises a polyinosinic acid strand and a polycytidylic acid strand (poly IC).

13. The complex of claim 11, wherein the at least one dsRBM is selected from a dsRBM of dsRNA dependent protein kinase (PKR), TRBP, PACT, Staufen, NFAR1, NFAR2, SPNR, RHA, and NREBP.

14. The complex of claim 13, wherein the dsRNA comprises a polyinosinic acid strand and a polycytidylic acid strand (poly IC).

15. The complex of claim 11, wherein the at least one dsRBM comprises a polypeptide sequence identical to amino acids 1-169 of human PKR as set forth as SEQ ID NO: 18.

16. The complex of claim 15, wherein the dsRNA comprises a polyinosinic acid strand and a polycytidylic acid strand (poly IC).

17. The complex of claim 7, wherein the double stranded RNA (dsRNA) binding domain is at least one dsRNA binding domain of human PKR as set forth in SEQ ID NO: 18, and wherein the target binding moiety is a single chain anti-PSMA antibody as set forth in SEQ ID NO: 20.

18. The complex of claim 17, wherein the dsRNA comprises a polyinosinic acid strand and a polycytidylic acid strand (poly IC).

19. The complex of claim 17, comprising a polypeptide identical to the sequence set forth as SEQ ID NO: 3.

20. The complex of claim 19, wherein the dsRNA comprises a polyinosinic acid strand and a polycytidylic acid strand (poly IC).

* * * * *

```
                            SEQUENCE LISTING

<160> NUMBER OF SEQ ID NOS: 21

<210> SEQ ID NO 1
<211> LENGTH: 517
<212> TYPE: PRT
<213> ORGANISM: Artificial Sequence
<220> FEATURE:
<223> OTHER INFORMATION: Recombinant polypeptide

<400> SEQUENCE: 1

Met Gly Ser Ser His His His His His Ser Ser Gly Leu Val Pro
1               5                   10                  15

Arg Gly Ser His Met Val Ser Lys Gly Glu Glu Leu Phe Thr Gly Val
            20                  25                  30

Val Pro Ile Leu Val Glu Leu Asp Gly Asp Val Asn Gly His Lys Phe
            35                  40                  45

Ser Val Ser Gly Glu Gly Glu Gly Asp Ala Thr Tyr Gly Lys Leu Thr
    50                  55                  60

Leu Lys Phe Ile Cys Thr Thr Gly Lys Leu Pro Val Pro Trp Pro Thr
65                  70                  75                  80

Leu Val Thr Thr Leu Thr Tyr Gly Val Gln Cys Phe Ser Arg Tyr Pro
                85                  90                  95

Asp His Met Lys Gln His Asp Phe Phe Lys Ser Ala Met Pro Glu Gly
                100                 105                 110

Tyr Val Gln Glu Arg Thr Ile Phe Phe Lys Asp Asp Gly Asn Tyr Lys
            115                 120                 125

Thr Arg Ala Glu Val Lys Phe Glu Gly Asp Thr Leu Val Asn Arg Ile
        130                 135                 140

Glu Leu Lys Gly Ile Asp Phe Lys Glu Asp Gly Asn Ile Leu Gly His
145                 150                 155                 160

Lys Leu Glu Tyr Asn Tyr Asn Ser His Asn Val Tyr Ile Met Ala Asp
                165                 170                 175

Lys Gln Lys Asn Gly Ile Lys Val Asn Phe Lys Ile Arg His Asn Ile
                180                 185                 190

Glu Asp Gly Ser Val Gln Leu Ala Asp His Tyr Gln Gln Asn Thr Pro
            195                 200                 205

Ile Gly Asp Gly Pro Val Leu Leu Pro Asp Asn His Tyr Leu Ser Thr
        210                 215                 220

Gln Ser Ala Leu Ser Lys Asp Pro Asn Glu Lys Arg Asp His Met Val
225                 230                 235                 240

Leu Leu Glu Phe Val Thr Ala Ala Gly Ile Thr Leu Gly Met Asp Glu
                245                 250                 255

Leu Tyr Lys Lys Ser Gly Gly Gly Ser Arg Arg Arg Arg Arg Arg Arg
                260                 265                 270

Arg Arg Gly Arg Lys Ala Ser Ala Glu Val Gln Leu Gln Gln Ser Gly
        275                 280                 285

Pro Glu Leu Val Lys Pro Gly Thr Ser Val Arg Ile Ser Cys Lys Thr
    290                 295                 300

Ser Gly Tyr Thr Phe Thr Glu Tyr Thr Ile His Trp Val Lys Gln Ser
305                 310                 315                 320
```

His Gly Lys Ser Leu Glu Trp Ile Gly Asn Ile Asn Pro Asn Asn Gly
            325                 330                 335

Gly Thr Thr Tyr Asn Gln Lys Phe Glu Asp Lys Ala Thr Leu Thr Val
        340                 345                 350

Asp Lys Ser Ser Ser Thr Ala Tyr Met Glu Leu Arg Ser Leu Thr Ser
    355                 360                 365

Glu Asp Ser Ala Val Tyr Tyr Cys Ala Ala Gly Trp Asn Phe Asp Tyr
370                 375                 380

Trp Gly Gln Gly Thr Thr Val Thr Val Ser Ser Gly Gly Gly Gly Ser
385                 390                 395                 400

Gly Gly Gly Gly Ser Gly Gly Gly Ser Asp Ile Val Met Thr Gln
            405                 410                 415

Ser His Lys Phe Met Ser Thr Ser Val Gly Asp Arg Val Ser Ile Ile
            420                 425                 430

Cys Lys Ala Ser Gln Asp Val Gly Thr Ala Val Asp Trp Tyr Gln Gln
            435                 440                 445

Lys Pro Gly Gln Ser Pro Lys Leu Leu Ile Tyr Trp Ala Ser Thr Arg
    450                 455                 460

His Thr Gly Val Pro Asp Arg Phe Thr Gly Ser Gly Ser Gly Thr Asp
465                 470                 475                 480

Phe Thr Leu Thr Ile Thr Asn Val Gln Ser Glu Asp Leu Ala Asp Tyr
            485                 490                 495

Phe Cys Gln Gln Tyr Asn Ser Tyr Pro Leu Thr Phe Gly Ala Gly Thr
            500                 505                 510

Met Leu Asp Leu Lys
        515

<210> SEQ ID NO 2
<211> LENGTH: 1554
<212> TYPE: DNA
<213> ORGANISM: Artificial Sequence
<220> FEATURE:
<223> OTHER INFORMATION: Recombinant polynucleotide

<400> SEQUENCE: 2

```
atgggcagca gccatcatca tcatcatcac agcagcggcc tggtgccgcg cggcagccat      60
atggtgagca agggcgagga gctgttcacc ggggtggtgc ccatcctggt cgagctggac     120
ggcgacgtaa acggccacaa gttcagcgtg tccggcgagg gcgagggcga tgccacctac     180
ggcaagctga ccctgaagtt catctgcacc accggcaagc tgcccgtgcc ctggcccacc     240
ctcgtgacca ccctgaccta cggcgtgcag tgcttcagcc gctaccccga ccacatgaag     300
cagcacgact tcttcaagtc cgccatgccc gaaggctacg tccaggagcg caccatcttc     360
ttcaaggacg acggcaacta caagacccgc gccgaggtga agttcgaggg cgacaccctg     420
gtgaaccgca tcgagctgaa gggcatcgac ttcaaggagg acggcaacat cctgggccac     480
aagctggagt acaactacaa cagccacaac gtctatatca tggccgacaa gcagaagaac     540
ggcatcaagg tgaacttcaa gatccgccac aacatcgagg acggcagcgt gcagctcgcc     600
gaccactacc agcagaacac ccccatcggc gacggccccg tgctgctgcc cgacaaccac     660
tacctgagca cccagtccgc cctgagcaaa gaccccaacg agaagcgcga tcacatggtc     720
ctgctggagt tcgtgaccgc cgccgggatc actctcggca tggacgagct gtacaagaaa     780
agcggcggtg gcggatcccg tcgtcgccgt cgtcgccgtc gcggccgcaa agcttccgca     840
gaggtgcagc tgcagcagtc aggacctgaa ctggtgaagc ctgggacttc agtgaggata     900
```

```
tcctgcaaga cttctggata cacattcact gaatatacca tacactgggt gaagcagagc    960
catggaaaga gccttgagtg gattggaaac atcaatccta acaatggtgg taccacctac   1020
aatcagaagt tcgaggacaa ggccacattg actgtagaca agtcctccag tacagcctac   1080
atggagctcc gcagcctaac atctgaggat tctgcagtct attattgtgc agctggttgg   1140
aactttgact actggggcca agggaccacg gtcaccgtct cctcaggtgg aggtggatca   1200
ggtggaggtg gatctggtgg aggtggatct gacattgtga tgacccagtc tcacaaattc   1260
atgtccacat cagtaggaga cagggtcagc atcatctgta aggccagtca agatgtgggt   1320
actgctgtag actggtatca acagaaacca ggacaatctc ctaaactact gatttattgg   1380
gcatccactc ggcacactgg agtccctgat cgcttcacag cagtggatc tgggacagac    1440 ttcactctca ccattactaa tgttcagtct gaagacttgg cagattattt ctgtcagcaa   1500
tataacagct atcccctcac gttcggtgct gggaccatgc tggacctgaa ataa         1554
```

<210> SEQ ID NO 3
<211> LENGTH: 446
<212> TYPE: PRT
<213> ORGANISM: Artificial Sequence
<220> FEATURE:
<223> OTHER INFORMATION: Recombinant polypeptide

<400> SEQUENCE: 3

```
Met Gly Ser Ser His His His His His His Ser Ser Gly Leu Val Pro
1               5                   10                  15

Arg Gly Ser His Met Met Ala Gly Asp Leu Ser Ala Gly Phe Phe Met
            20                  25                  30

Glu Glu Leu Asn Thr Tyr Arg Gln Lys Gln Gly Val Val Leu Lys Tyr
        35                  40                  45

Gln Glu Leu Pro Asn Ser Gly Pro Pro His Asp Arg Arg Phe Thr Phe
    50                  55                  60

Gln Val Ile Ile Asp Gly Arg Glu Phe Pro Glu Gly Glu Gly Arg Ser
65                  70                  75                  80

Lys Lys Glu Ala Lys Asn Ala Ala Ala Lys Leu Ala Val Glu Ile Leu
                85                  90                  95

Asn Lys Glu Lys Lys Ala Val Ser Pro Leu Leu Leu Thr Thr Thr Asn
            100                 105                 110

Ser Ser Glu Gly Leu Ser Met Gly Asn Tyr Ile Gly Leu Ile Asn Arg
        115                 120                 125

Ile Ala Gln Lys Lys Arg Leu Thr Val Asn Tyr Glu Gln Cys Ala Ser
    130                 135                 140

Gly Val His Gly Pro Glu Gly Phe His Tyr Lys Cys Lys Met Gly Gln
145                 150                 155                 160

Lys Glu Tyr Ser Ile Gly Thr Gly Ser Thr Lys Gln Glu Ala Lys Gln
                165                 170                 175

Leu Ala Ala Lys Leu Ala Tyr Leu Gln Ile Leu Ser Glu Ser Gly Gly
            180                 185                 190

Gly Gly Ser Arg Arg Arg Arg Arg Arg Arg Gly Arg Lys Ala Ser
        195                 200                 205

Ala Glu Val Gln Leu Gln Gln Ser Gly Pro Glu Leu Val Lys Pro Gly
    210                 215                 220

Thr Ser Val Arg Ile Ser Cys Lys Thr Ser Gly Tyr Thr Phe Thr Glu
225                 230                 235                 240

Tyr Thr Ile His Trp Val Lys Gln Ser His Gly Lys Ser Leu Glu Trp
                245                 250                 255
```

```
Ile Gly Asn Ile Asn Pro Asn Gly Gly Thr Thr Tyr Asn Gln Lys
            260                 265                 270

Phe Glu Asp Lys Ala Thr Leu Thr Val Asp Lys Ser Ser Thr Ala
            275                 280                 285

Tyr Met Glu Leu Arg Ser Leu Thr Ser Glu Asp Ser Ala Val Tyr Tyr
            290                 295                 300

Cys Ala Ala Gly Trp Asn Phe Asp Tyr Trp Gly Gln Gly Thr Thr Val
305                 310                 315                 320

Thr Val Ser Ser Gly Gly Gly Ser Gly Gly Gly Ser Gly Gly
            325                 330                 335

Gly Gly Ser Asp Ile Val Met Thr Gln Ser His Lys Phe Met Ser Thr
            340                 345                 350

Ser Val Gly Asp Arg Val Ser Ile Ile Cys Lys Ala Ser Gln Asp Val
            355                 360                 365

Gly Thr Ala Val Asp Trp Tyr Gln Lys Pro Gly Gln Ser Pro Lys
            370                 375                 380

Leu Leu Ile Tyr Trp Ala Ser Thr Arg His Thr Gly Val Pro Asp Arg
385                 390                 395                 400

Phe Thr Gly Ser Gly Ser Gly Thr Asp Phe Thr Leu Thr Ile Thr Asn
            405                 410                 415

Val Gln Ser Glu Asp Leu Ala Asp Tyr Phe Cys Gln Gln Tyr Asn Ser
            420                 425                 430

Tyr Pro Leu Thr Phe Gly Ala Gly Thr Met Leu Asp Leu Lys
            435                 440                 445

<210> SEQ ID NO 4
<211> LENGTH: 1338
<212> TYPE: DNA
<213> ORGANISM: Artificial Sequence
<220> FEATURE:
<223> OTHER INFORMATION: Recombinant polynucleotide

<400> SEQUENCE: 4
atgggcagca gccatcatca tcatcatcac agcagcggcc tggtgccgcg cggcagccat      60
atgatggctg gtgatctttc agcaggtttc ttcatggagg aacttaatac ataccgtcag     120
aagcagggag tagtacttaa atatcaagaa ctgcctaatt caggacctcc acatgatagg     180
aggtttacat ttcaagttat aatagatgga agagaatttc agaaggtgaa ggtagatca     240 aagaaggaag caaaaaatgc cgcagccaaa ttagctgttg agatacttaa taaggaaaag     300
aaggcagtta gtccttttat attgacaaca acgaattctt cagaaggatt atccatgggg     360
aattacatag gccttatcaa tagaattgcc cagaagaaaa gactaactgt aaattatgaa     420
cagtgtgcat cggggggtgca tgggccagaa ggatttcatt ataaatgcaa aatgggacag     480
aaagaatata gtattggtac aggttctact aaacaggaag caaaacaatt ggcggccaaa     540
ctggcctatc tgcagatctt atcggagagc ggcggtggcg gatcccgtcg tcgccgtcgt     600
cgccgtcgcg gccgcaaagc ttccgcagag gtgcagctgc agcagtcagg acctgaactg     660
gtgaagcctg ggacttcagt gaggatatcc tgcaagactt ctggatacac attcactgaa     720
tataccatac actgggtgaa gcagagccat ggaaagagcc ttgagtggat tgaaacatc      780 aatcctaaca atggtggtac cacctacaat cagaagttcg aggacaaggc cacattgact     840
gtagacaagt cctccagtac agcctacatg agctccgca gcctaacatc tgaggattct     900
gcagtctatt attgtgcagc tggttggaac tttgactact ggggccaagg gaccacggtc     960
```

```
accgtctcct caggtggagg tggatcaggt ggaggtggat ctggtggagg tggatctgac    1020
attgtgatga cccagtctca caaattcatg tccacatcag taggagacag ggtcagcatc    1080
atctgtaagg ccagtcaaga tgtgggtact gctgtagact ggtatcaaca gaaaccagga    1140
caatctccta aactactgat ttattgggca tccactcggc acactggagt ccctgatcgc    1200
ttcacaggca gtggatctgg gacagacttc actctcacca ttactaatgt tcagtctgaa    1260
gacttggcag attatttctg tcagcaatat aacagctatc ccctcacgtt cggtgctggg    1320
accatgctgg acctgaaa                                                  1338
```

```
<210> SEQ ID NO 5
<211> LENGTH: 14
<212> TYPE: PRT
<213> ORGANISM: Artificial Sequence
<220> FEATURE:
<223> OTHER INFORMATION: Synthetic oligopeptide

<400> SEQUENCE: 5

Gly Ser Arg Arg Arg Arg Arg Arg Arg Gly Arg Lys Ala
1               5                   10
```

```
<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 6
atgaccaaca agtgtctcct cc                                              22
```

```
<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
gctcatggaa agagctgtag tg                                              22
```

```
<210> SEQ ID NO 8
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 8
gagccacatc gctcagac                                                   18
```

```
<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
cttctcatgg ttcacaccc                                                  19
```

```
<210> SEQ ID NO 10
<211> LENGTH: 28
<212> TYPE: DNA
```

```
<213> ORGANISM: Artificial Sequence
<220> FEATURE:
<223> OTHER INFORMATION: Synthetic oligonucleotide

<400> SEQUENCE: 10
tttactcgag cggaggtgca gctgcagc                                          28

<210> SEQ ID NO 11
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 11
ttttgctcag cgccgttaca ggtccagcca tg                                     32

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 12
ttttcatatg gtgagcaagg gcg                                               23

<210> SEQ ID NO 13
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 13
taaggatccg ccaccgccgc ttttcttgta cagc                                   34

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 14
tttcatatga tggctggtga tc                                                22

<210> SEQ ID NO 15
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 15
ttaggatccg ccaccgccgc tctccgataa gatctgcag                              39

<210> SEQ ID NO 16
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 16
gatcccgtcg tcgccgtcgt cgccgtcgcg gccgcaa                                37
```

<210> SEQ ID NO 17
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 17
agctttgcgg ccgcgacggc gacgacggcg acgacgg                           37

<210> SEQ ID NO 18
<211> LENGTH: 169
<212> TYPE: PRT
<213> ORGANISM: Homo sapiens

<400> SEQUENCE: 18

Met Met Ala Gly Asp Leu Ser Ala Gly Phe Phe Met Glu Glu Leu Asn
1               5                   10                  15

Thr Tyr Arg Gln Lys Gln Gly Val Val Leu Lys Tyr Gln Glu Leu Pro
            20                  25                  30

Asn Ser Gly Pro Pro His Asp Arg Arg Phe Thr Phe Gln Val Ile Ile
        35                  40                  45

Asp Gly Arg Glu Phe Pro Glu Gly Glu Gly Arg Ser Lys Lys Glu Ala
    50                  55                  60

Lys Asn Ala Ala Ala Lys Leu Ala Val Glu Ile Leu Asn Lys Glu Lys
65                  70                  75                  80

Lys Ala Val Ser Pro Leu Leu Leu Thr Thr Thr Asn Ser Ser Glu Gly
                85                  90                  95

Leu Ser Met Gly Asn Tyr Ile Gly Leu Ile Asn Arg Ile Ala Gln Lys
            100                 105                 110

Lys Arg Leu Thr Val Asn Tyr Glu Gln Cys Ala Ser Gly Val His Gly
        115                 120                 125

Pro Glu Gly Phe His Tyr Lys Cys Lys Met Gly Gln Lys Glu Tyr Ser
    130                 135                 140

Ile Gly Thr Gly Ser Thr Lys Gln Glu Ala Lys Gln Leu Ala Ala Lys
145                 150                 155                 160

Leu Ala Tyr Leu Gln Ile Leu Ser Glu
                165

<210> SEQ ID NO 19
<211> LENGTH: 507
<212> TYPE: DNA
<213> ORGANISM: Homo sapiens

<400> SEQUENCE: 19
atgatggctg gtgatctttc agcaggtttc ttcatggagg aacttaatac ataccgtcag     60
aagcagggag tagtacttaa atatcaagaa ctgcctaatt caggacctcc acatgatagg    120
aggtttacat ttcaagttat aatagatgga agagaatttc cagaaggtga aggtagatca    180
aagaaggaag caaaaaatgc cgcagccaaa ttagctgttg agatacttaa taaggaaaag    240
aaggcagtta gtcctttatt attgacaaca acgaattctt cagaaggatt atccatgggg    300
aattacatag gccttatcaa tagaattgcc agaagaaaaa gactaactgt aaattatgaa    360
cagtgtgcat cgggggtgca tgggccagaa ggatttcatt ataaatgcaa aatgggacag    420
aaagaatata gtattggtac aggttctact aaacaggaag caaaacaatt ggcggccaaa    480
ctggcctatc tgcagatctt atcggag                                       507

<210> SEQ ID NO 20
<211> LENGTH: 237
<212> TYPE: PRT
<213> ORGANISM: Artificial Sequence
<220> FEATURE:
<223> OTHER INFORMATION: Synthetic polypeptide

<400> SEQUENCE: 20

```
Glu Val Gln Leu Gln Gln Ser Gly Pro Glu Leu Val Lys Pro Gly Thr
1               5                   10                  15
Ser Val Arg Ile Ser Cys Lys Thr Ser Gly Tyr Thr Phe Thr Glu Tyr
            20                  25                  30
Thr Ile His Trp Val Lys Gln Ser His Gly Lys Ser Leu Glu Trp Ile
        35                  40                  45
Gly Asn Ile Asn Pro Asn Asn Gly Gly Thr Thr Tyr Asn Gln Lys Phe
    50                  55                  60
Glu Asp Lys Ala Thr Leu Thr Val Asp Lys Ser Ser Ser Thr Ala Tyr
65                  70                  75                  80
Met Glu Leu Arg Ser Leu Thr Ser Glu Asp Ser Ala Val Tyr Tyr Cys
                85                  90                  95
Ala Ala Gly Trp Asn Phe Asp Tyr Trp Gly Gln Gly Thr Thr Val Thr
            100                 105                 110
Val Ser Ser Gly Gly Gly Gly Ser Gly Gly Gly Gly Ser Gly Gly Gly
        115                 120                 125
Gly Ser Asp Ile Val Met Thr Gln Ser His Lys Phe Met Ser Thr Ser
    130                 135                 140
Val Gly Asp Arg Val Ser Ile Ile Cys Lys Ala Ser Gln Asp Val Gly
145                 150                 155                 160
Thr Ala Val Asp Trp Tyr Gln Gln Lys Pro Gly Gln Ser Pro Lys Leu
                165                 170                 175
Leu Ile Tyr Trp Ala Ser Thr Arg His Thr Gly Val Pro Asp Arg Phe
            180                 185                 190
Thr Gly Ser Gly Ser Gly Thr Asp Phe Thr Leu Thr Ile Thr Asn Val
        195                 200                 205
Gln Ser Glu Asp Leu Ala Asp Tyr Phe Cys Gln Gln Tyr Asn Ser Tyr
    210                 215                 220
Pro Leu Thr Phe Gly Ala Gly Thr Met Leu Asp Leu Lys
225                 230                 235
```

<210> SEQ ID NO 21
<211> LENGTH: 711
<212> TYPE: DNA
<213> ORGANISM: Artificial Sequence
<220> FEATURE:
<223> OTHER INFORMATION: Synthetic polynucleotide

<400> SEQUENCE: 21

```
gaggtgcagc tgcagcagtc aggacctgaa ctggtgaagc ctgggacttc agtgaggata      60
tcctgcaaga cttctggata cacattcact gaatatacca tacactgggt gaagcagagc     120
catggaaaga gccttgagtg gattggaaac atcaatccta acaatggtgg taccacctac     180
aatcagaagt tcgaggacaa ggccacattg actgtagaca agtcctccag tacagcctac     240
atggagctcc gcagcctaac atctgaggat tctgcagtct attattgtgc agctggttgg     300
aactttgact actggggcca aggaccacg gtcaccgtct cctcaggtgg aggtggatca     360
ggtggaggtg gatctggtgg aggtggatct gacattgtga tgacccagtc tcacaaattc     420
```

-continued

```
atgtccacat cagtaggaga cagggtcagc atcatctgta aggccagtca agatgtgggt    480
actgctgtag actggtatca acagaaacca ggacaatctc ctaaactact gatttattgg    540
gcatccactc ggcacactgg agtccctgat cgcttcacag gcagtggatc tgggacagac    600
ttcactctca ccattactaa tgttcagtct gaagacttgg cagattattt ctgtcagcaa    660
tataacagct atcccctcac gttcggtgct gggaccatgc tggacctgaa a             711
```